US008066983B2

(12) United States Patent
Wimmer et al.

(10) Patent No.: US 8,066,983 B2
(45) Date of Patent: Nov. 29, 2011

(54) ATTENUATED POLIOVIRUS

(75) Inventors: Eckard Wimmer, E. Setauket, NY (US); Jeronimo Cello, Port Jefferson, NY (US); Aniko Paul, Setauket, NY (US); Hidemi Toyoda, E. Setauket, NY (US); Jiang Yin, Port Jefferson, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

(21) Appl. No.: 12/405,068

(22) Filed: Mar. 16, 2009

(65) Prior Publication Data

US 2009/0246216 A1 Oct. 1, 2009

Related U.S. Application Data

(60) Provisional application No. 61/036,925, filed on Mar. 14, 2008.

(51) Int. Cl.
*A61K 39/12* (2006.01)
*C12P 19/33* (2006.01)

(52) U.S. Cl. .................................... 424/93.1; 424/217.1

(58) Field of Classification Search ........................ None
See application file for complete search history.

(56) References Cited

U.S. PATENT DOCUMENTS 6,464,972 B1 10/2002 Gromeier

OTHER PUBLICATIONS

Berwin, B., Reed, R.C., Nicchitta, C.V. "Virally induced lytic cell death elicits the release of immunogenic GRP94/gp96". J Biol Chem (2001); vol. 276:24, pp. 21083-21088.
Cello, J., Paul, A.V., Wimmer, E. "Chemical synthesis of poliovirus cDNA: generation of infectious virus in the absence of natural template". Science (2002); vol. 297: pp. 1016-1018.
Cello, J., Toyoda, H., DeJesus, N., Wimmer, E. "Growth phenotypes and biosafety profiles in poliovirus receptor transgenic mice of recombinant oncolytic polio/human rhinoviruses". J. Med. Virol. (2008) ;vol. 80: pp. 352-359.
Coffey, M.C., Strong, J.E., Forsyth, P.A., Lee, P.W. "Reovirus therapy of tumors with activated Ras pathway". Science (1998); vol. 282: pp. 1332-1334.
DeJesus, N., Franco, D., Paul, A., Wimmer, E., Cello, J. "Mutation of a single conserved nucleotide between the cloverleaf and internal ribosome entry site attenuates poliovirus neurovirulence". J Virol (2005); vol. 79:22, pp. 14235-14243.
Gromeier, M., Alexander, L., Wimmer, E. "Internal ribosomal entry site substitution eliminates neurovirulence in intergeneric poliovirus recombinants". Proc Nati Acad Sci U S A (1996); vol. 93: pp. 2370-2375.
Gromeier, M., Bossed, B., Arita, M., Nomoto, A., Wimmer, E. "Dual stem loops within the poliovirus internal ribosomal entry site control neurovirulence". J Virol (1999); vol. 73:2, pp. 958-964.
Gromeier, M., Lachmann, S., Rosenfeld, M.R., Gutin, P.H., Wimmer, E. "Intergeneric poliovirus recombinants for the treatment of malignant glioma". Proc Natl Acad Sci U S A (2000); vol. 97:12, pp. 6803-6808.
Katzenstein, H.M., Cohn, S.L. "Advances in the diagnosis and treatment of neuroblastoma". Curr Opin Oncol (1998); vol. 10: pp. 43-51.
Kirn, D., Martuza, R.L., Zwiebel, J. "Replication-selective virotherapy for cancer: biological principles, risk management, and future directions". Nat Med (2001); vol. 7:7, pp. 781-787.
Koike, S., Taya, C., Kurata, T., et al. "Transgenic mice susceptible to poliovirus". Proc Natl Acad Sci U S A (1991); vol. 88: pp. 951-955.
Kushner, B.H., Cheung, N.K., Kramer, K., Heller, G., Jhanwar, S.C. "Neuroblastoma and treatment-related myelodysplasia/leukemia: the Memorial Sloan-Kettering experience and a literature review". J Clin Oncol (1998); vol. 16: pp. 3880-3889.
Matthay, K.K., Villablanca, J.G., Seeger, R.C., et al. "Treatment of high-risk neuroblastoma with intensive chemotherapy, radiotherapy, autologous bone marrow transplantation, and 13-cis-retinoic acid". Children's Cancer Group. N Engl J Med (1999); vol. 341:16, pp. 1165-1173.
Mohr, I. "To replicate or not to replicate: achieving selective oncolytic virus replication in cancer cells through translational control". Oncogene (2005); vol. 24: pp. 7697-7709.
Mueller, S., Wimmer, E. "Recruitment of nectin-3 to cell-cell junctions through trans-heterophilic interaction with CD155, a vitronectin and poliovirus receptor that localizes to a(v)h3 integrin-containing membrane microdomains". J Biol Chem (2003); vol. 278:33, pp. 31251-31260.
Mueller, S., Wimmer, E., Cello, J. "Poliovirus and poliomyelitis: a tale of guts, brains, and an accidental event". Virus Res (2005); vol. 111: pp. 175-193.
Nakamura, H., Kasuya, H., Mullen, J.T., et al. "Regulation of herpes simplex virus g(1)34.5 expression and oncolysis of diffuse liver metastases by Myb34.5". J Clin Invest (2002); vol. 109: pp. 871-882.
Nemunaitis, J., Ganly, I., Khuri, F., et al. "Selective replication and oncolysis in p53 mutant tumors with ONYX-015, an E1B-55kD gene-deleted adenovirus, in patients with advanced head and neck cancer: a phase II trial". Cancer Res (2000); vol. 60: pp. 6359-6366.
Obuchi, M., Fernandez, M., Barber, G.N. "Development of recombinant vesicular stomatitis viruses that exploit defects in host defense to augment specific oncolytic activity". J Virol (2003); vol. 77:16, pp. 8843-8856.
Ochiai, H., Moore, S.A., Archer, G.E., et al. "Treatment of intracerebral neoplasia and neoplastic meningitis with regional delivery of oncolytic recombinant poliovirus". Clin Cancer Res (2004); vol. 10: pp. 4831-4838.
Ochiai, H., Campbell, S.A., Archer, G.E, et al. "Targeted therapy for glioblastoma multiforme neoplastic meningitis with intrathecal delivery of an oncolytic recombinant poliovirus". Clin Cancer Res (2006); vol. 12: pp. 1349-1354.
Parato, K.A., Senger, D., Forsyth, P.A., Bell, J.C. "Recent progress in the battle between oncolytic viruses and tumours". Nat Rev Cancer (2005); vol. 5: pp. 965-976.

(Continued)

*Primary Examiner* — Bao Li
(74) *Attorney, Agent, or Firm* — Kenyon & Kenyon LLP

(57) ABSTRACT

A novel and stable attenuated poliovirus, which replicates in neuroblastoma cells, is produced by engineering an indigenous replication element (cre), into the 5' non-translated genomic region and inactivating the native cre element located in the coding region of 2C (mono-crePV). The stably attenuated poliovirus replicates in a neuroblastoma model (Neuro-2a$^{CD155}$ tumors) expressing CD155, the poliovirus receptor, and is effective for oncolytic treatment and cure of solid tumors, such as neuroblastoma.

10 Claims, 8 Drawing Sheets

OTHER PUBLICATIONS

Paul, A.V. "Possible unifying mechanism of picornavirus genome replication. In: Semler BL, Wimmer E, editors. Molecular biology of picornaviruses". Washington (DC): ASM Press; (2002). pp. 227-246.

Paul, A.V., Yin, J., Mugavero, J., et al. "A "slide-back" mechanism for the initiation of protein-primed RNA synthesis by the RNA polymerase of poliovirus". J Biol Chem (2003); vol. 278: pp. 43951-43960.

Pincus, S.E., Diamond, D.C., Emini, E.A., Wimmer E. "Guanidine-selected mutants of poliovirus: mapping of point mutations to polypeptide 2C". J Virol (1986); vol. 57: pp. 638-646.

Porosnicu, M., Mian, A., Barber, G.N. "The oncolytic effect of recombinant vesicular stomatitis virus is enhanced by expression of the fusion cytosine deaminase/uracil phosphoribosyltransferase suicide gene". Cancer Res (2003); vol. 63:pp. 8366-8376.

Reed, L.J., Muench, H. "A simple method of estimating fifty per cent endpoint". Am J Hyg (1938); vol. 27: pp. 493-497.

Rieder, E., Paul, A.V., Kim, D.W., van Boom, J.H., Wimmer, E. "Genetic and biochemical studies of poliovirus cis-acting replication element cre in relation to VPg uridylylation". J Virol (2000); vol. 74: pp. 10371-10380.

Ring, C.J. "Cytolytic viruses as potential anti-cancer agents". J Gen Virol (2002); vol. 83: pp. 491-502.

Shiroki, K., Ishii T., Aoki, T., Kobashi M., Ohka, S., Nomoto, A. "A new cis-acting element for RNA replication within the 5' noncoding region of poliovirus type 1 RNA". J Virol (1995); vol. 69: pp. 6825-6832.

Solecki, D., Schwarz, S., Wimmer, E., Lipp, M., Bernhardt, G. "The promoters for human and monkey poliovirus receptors. Requirements for basic and cell type-specific activity". J Biol Chem (1997); vol. 272: pp. 5579-5586.

Thorne, S.H., Hermiston, T., Kim, D. "Oncolytic virotherapy: approaches to tumor targeting and enhancing antitumor effects". Semin Oncol (2005); vol. 32: pp. 537-548.

Toyoda, H., Ido, M., Hayashi, T., et al. "Experimental treatment of human neuroblastoma using live-attenuated poliovirus". Int J Oncol (2004); vol. 24: pp. 49-58.

Van Der Wert, S., Bradley, J., Wimmer, E., Studier, F.W., Dunn, J.J. "Synthesis of infectious poliovirus RNA by purified T7 RNA polymerase". Proc Natl Acad Sci U S A (1986); vol. 83: pp. 2330-2334.

Wahby, A.F. "Combined cell culture enzyme-linked immunosorbent assay for quantification of poliovirus neutralization-relevant antibodies". Clin Diagn Lab Immunol (2000); vol. 7: pp. 915-919.

Weinstein, J.L., Katzenstein, H.M., Cohn, S.L. "Advances in the diagnosis and treatment of neuroblastoma". Oncologist (2003); vol. 8: pp. 278-292.

Yin, J., Paul, A.V., Wimmer, E., Rieder E. "Functional dissection of a poliovirus cis-acting replication element [PV-cre (2C)]: analysis of single- and dual-cre viral genomes and proteins that bind specifically to PV-cre RNA". J Virol (2003); vol. 77: pp. 5152-5166.

Young, L.S., Searle, P.F., Onion, D., Mautner, V. "Viral gene therapy strategies: from basic science to clinical application". J Pathol (2006); vol. 208: pp. 299-318.

Borman, Andrew M., "Sequences within a poliovirus internal ribosome entry segment control viral RNA synthesis", EMBO Journal (1994), vol. 13:13, pp. 3149-3157.

Toyoda, H. et al., "Oncolytic treatment and cure of neuroblastoma by a novel attenuated poliovirus in a novel poliovirus-susceptible animal model", Cancer Res (2007) vol. 67:6, pp. 2857-2864.

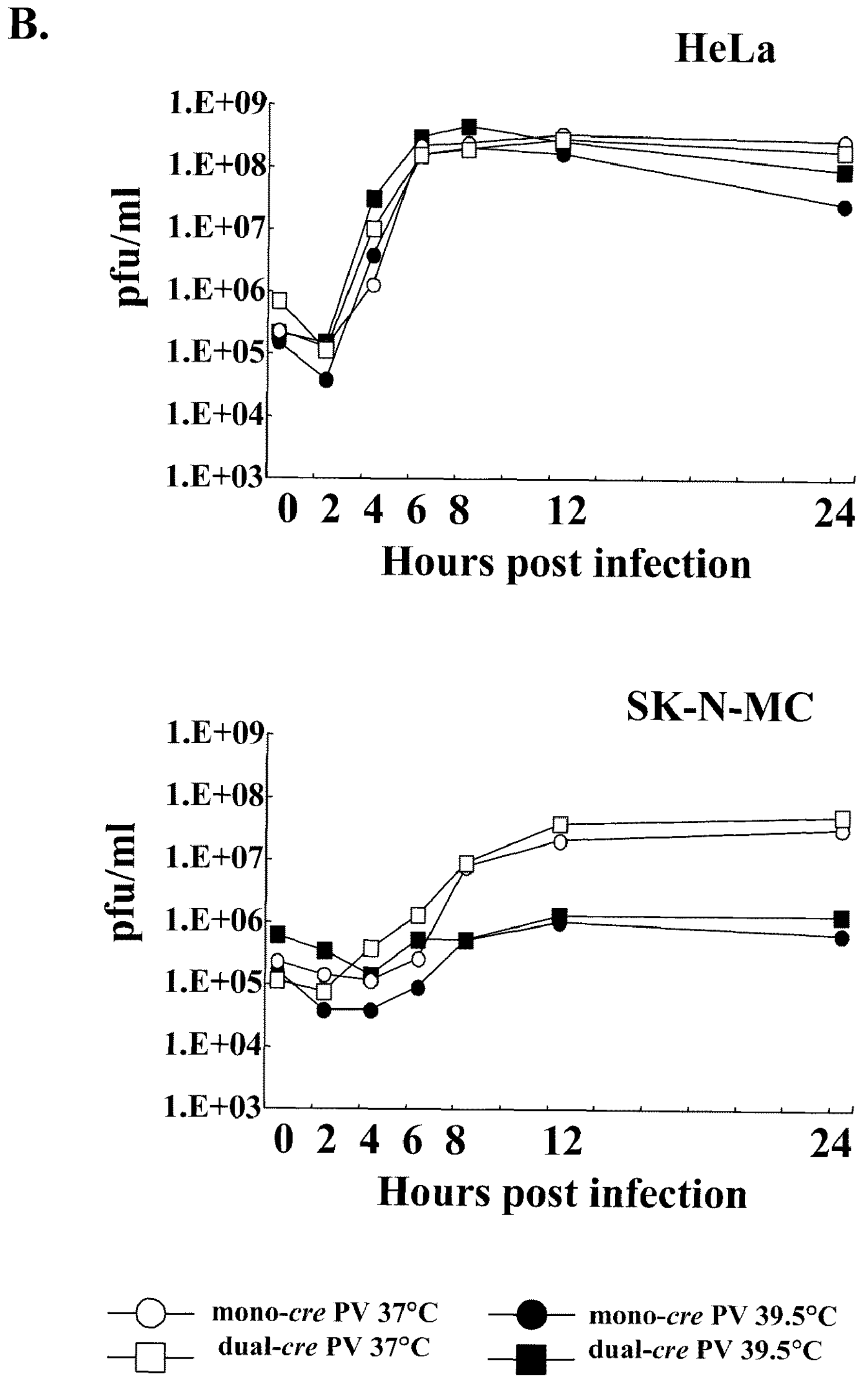
Fig. 1 (con't.)

A.

B.

SEQUENCE LISTING

```
<160> NUMBER OF SEQ ID NOS: 3

<210> SEQ ID NO 1
<211> LENGTH: 7570
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (1)..(88)
<223> OTHER INFORMATION: cloverleaf
<220> FEATURE:
<221> NAME/KEY: misc_feature
<222> LOCATION: (109)..(169)
<223> OTHER INFORMATION: PVcre(2C)
<220> FEATURE:
<221> NAME/KEY: mutation
<222> LOCATION: (203)..(203)
<223> OTHER INFORMATION: A133G
<220> FEATURE:
<221> NAME/KEY: misc_feature
<222> LOCATION: (4514)..(4574)
<223> OTHER INFORMATION: PVcre(2C) - inactivated

<400> SEQUENCE: 1

ttaaaacagc tctggggttg tacccacccc agaggcccac gtggcggcta gtactccggt     60

attgcggtac ccttgtacgc ctgttttata ctcccttccc gctagcacta ttaacaacta    120

catacagttc aagagcaaac accgtattga accagtatgt ttgctagtag ctagcttaga    180

cgcacaaaac caagttcaat aggagggggt acaaaccagt accaccacga acaagcactt    240

ctgtttcccc ggtgatgtcg tatagactgc ttgcgtggtt gaaagcgacg gatccgttat    300
```

-continued

```
ccgcttatgt acttcgagaa gcccagtacc acctcggaat cttcgatgcg ttgcgctcag    360
cactcaaccc cagagtgtag cttaggctga tgagtctgga catccctcac cggtgacggt    420
ggtccaggct gcgttggcgg cctacctatg gctaacgcca tgggacgcta gttgtgaaca    480
aggtgtgaag agcctattga gctacataag aatcctccgg cccctgaatg cggctaatcc    540
caacctcgga gcaggtggtc acaaaccagt gattggcctg tcgtaacgcg caagtccgtg    600
gcggaaccga ctactttggg tgtccgtgtt tccttttatt ttattgtggc tgcttatggt    660
gacaatcaca gattgttatc ataaagcgaa ttggattggc catccggtga aagtgagact    720
cattatctat ctgtttgctg gatccgctcc attgagtgtg tttactctaa gtacaatttc    780
aacagttatt tcaatcagac aattgtatca taatgggtgc tcaggtttca tcacagaaag    840
tgggcgcaca tgaaaactca aatagagcgt atggtagttc taccattaat tacaccacca    900
ttaattatta tagagattca gctagtaacg cggcttcgaa acaggacttc tctcaagacc    960
cttccaagtt caccgagccc atcaaggatg tcctgataaa aacagcccca atgctaaact   1020
cgccaaacat agaggcttgc gggtatagcg atagagtact gcaattaaca ctgggaaact   1080
ccactataac cacacaggag gcggctaatt cagtagtcgc ttatgggcgt tggcctgaat   1140
atctgaggga cagcgaagcc aatccagtgg accagccgac agaaccagac gtcgctgcat   1200
gcaggtttta tacgctagac accgtgtctt ggacgaaaga gtcgcgaggg tggtggtgga   1260
agttgcctga tgcactgagg gacatgggac tctttgggca aaatatgtac taccactacc   1320
taggtaggtc cgggtacacc gtgcatgtac agtgtaacgc ctccaaattc caccaggggg   1380
cactaggggt attcgccgta ccagagatgt gtctggccgg ggatagcaac accactacca   1440
tgcacaccag ctatcaaaat gccaatcctg gcgagaaagg aggcactttc acgggtacgt   1500
tcactcctga caacaaccag acatcacctg cccgcaggtt ctgcccggtg gattacctcc   1560
ttggaaatgg cacgttgttg gggaatgcct ttgtgttccc gcaccagata ataaacctac   1620
ggaccaacaa ctgtgctaca ctggtactcc cttacgtgaa ctccctctcg atagatagta   1680
tggtaaagca caataattgg ggaattgcaa tattaccatt ggccccatta aattttgcta   1740
gtgagtcctc cccagagatt ccaatcacct tgaccatagc ccctatgtgc tgtgagttca   1800
atggattaag aaacatcacc ctgccacgct tacagggcct gccggtcatg aacacccctg   1860
gtagcaatca atatcttact gcagacaact tccagtcacc gtgtgcgctg cctgaatttg   1920
atgtgacccc acctattgac atacccggtg aagtaaagaa catgatggaa ttggcagaaa   1980
tcgacaccat gattcccttt gacttaagtg ccacaaaaaa gaacaccatg gaaatgtata   2040
gggttcggtt aagtgacaaa ccacatacag acgatcccat actctgcctg tcactctctc   2100
cagcctcaga tcctaggttg tcacatacta tgcttggaga aatcctaaat tactacacac   2160
actgggcagg atccctgaag ttcacgtttc tgttctgtgg atccatgatg gcaactggca   2220
aactgttggt gtcatacgcg cctcctggag ccgacccacc aaagaagcgt aaggaggcga   2280
tgttgggaac acatgtgatc tgggacatag gactgcagtc ctcatgtact atggtagtgc   2340
catggattag caacaccacg tatcggcaaa ccatagatga tagtttcacc gaaggcggat   2400
acatcagcgt cttctaccaa actagaatag tcgtccctct ttcgacaccc agagagatgg   2460
acatccttgg ttttgtgtca gcgtgtaatg acttcagcgt gcgcttgttg cgagatacca   2520
cacatataga gcaaaaagcg ctagcacagg ggttaggtca gatgcttgaa agcatgattg   2580
acaacacagt ccgtgaaacg gtgggggcgg caacatctag agacgctctc ccaaacactg   2640
aagccagtgg accaacacac tccaaggaaa ttccggcact caccgcagtg gaaactgggg   2700
```

ccacaaatcc actagtccct tctgatacag tgcaaaccag acatgttgta caacataggt 2760
caaggtcaga gtctagcata gagtctttct tcgcgcgggg tgcatgcgtg accattatga 2820
ccgtggataa cccagcttcc accacgaata aggataagct tttgcagtg tggaagatca 2880 cttataaaga tactgtccag ttacggagga aattggagtt cttcacctat tctagatttg 2940
atatggaact tacctttgtg gttactgcaa atttcactga gactaacaat ggccatgcat 3000
taaatcaagt gtaccaaatt atgtacgtac caccaggcgc tccagtgccc gaaaaatggg 3060
acgactacac atggcaaacc tcatcaaatc catcaatctt ttacacctac gggacagctc 3120
cagcccggat ctcggtaccg tatgttggta tttcgaacgc ctattcacac ttttacgacg 3180
gtttttccaa agtaccactg aaggaccagt cggcagcact aggtgactcc ctttatggtg 3240
cagcatctct aaatgacttc ggtattttgg ctgttagagt agtcaatgat cacaacccga 3300
ccaaggtcac ctccaaaatc agagtgtatc taaaacccaa acacatcaga gtctggtgcc 3360
cgcgtccacc gagggcagtg gcgtactacg gccctggagt ggattacaag gatggtacgc 3420
ttacacccct ctccaccaag gagctcacca catatggatt cggacaccaa aacaaagcgg 3480
tgtacactgc aggttacaaa atttgcaact accacttggc cactcaggat gatttgcaaa 3540
acgcagtgaa cgtcatgtgg agtagagacc tcttagtcac agaatcaaga gcccagggca 3600
ccgattcaat cgcaaggtgc aattgcaacg caggggtgta ctactgcgag tctagaagga 3660
aatactaccc agtatccttc gttggcccaa cgttccagta catggaggct aataactatt 3720
acccagctag gtaccagtcc catatgctca ttggccatgg attcgcatct ccaggggatt 3780
gtggtggcat actcagatgt caccacgggg tgatagggat cattactgct ggtggagaag 3840
ggttggttgc attttcagac attagagact tgtatgccta cgaagaagaa gccatggaac 3900
aaggcctcac caattacata gagtcacttg gggccgcatt tggaagtgga tttactcagc 3960
agattagcga caaaataaca gagttgacca atatggtgac cagtaccatc actgaaaagc 4020
tacttaagaa cttgatcaag atcatatcct cactagttat tataactagg aactatgaag 4080
acaccacaac agtgctcgct accctggccc ttcttgggtg tgatgcttca ccatggcagt 4140
ggcttagaaa gaaagcatgc gatgttctgg agatacctta tgtcatcaag caaggtgaca 4200
gttggttgaa gaagtttact gaagcatgca acgcagctaa gggactggag tgggtgtcaa 4260
acaaaatctc aaaattcatt gattggctca aggagaaaat tatcccacaa gctagagata 4320
agttggaatt tgtaacaaaa cttagacaac tagaaatgct ggaaaaccaa atctcaacta 4380
tacaccaatc atgccctagt caggaacacc aggaaattct attcaataat gtcagatggt 4440
tatccatcca gtctaagagg tttgcccctc tttacgcagt ggaagccaaa agaatacaga 4500
aactcgagca tactattaac aactacatac aatttaagag ccaacaccgt atcgaaccag 4560
tatgtttgct agtacatggc agccccggaa caggtaaatc tgtagcaacc aacctgattg 4620
ctagagccat agctgaaaga gaaaacacgt ccacgtactc gctacccccg gatccatcac 4680
acttcgacgg atacaaacaa cagggagtgg tgattatgga cgacctgaat caaaacccag 4740
atggtgcgga catgaagctg ttctgtcaga tggtatcaac agtggagttt ataccaccca 4800
tggcatccct ggaggagaaa ggaatcctgt ttacttcaaa ttacgttcta gcatccacaa 4860
actcaagcag aatttccccc cccactgtgg cacacagtga cgcgttagcc aggcgctttg 4920
cgttcgacat ggacattcag gtcatgaatg agtattctag agatgggaaa ttgaacatgg 4980
ccatggctac tgaaatgtgt aagaactgtc accaaccagc aaactttaag agatgctgtc 5040
ctttagtgtg tggtaaggca attcaattaa tggacaaatc ttccagagtt agatacagta 5100

-continued ttgaccagat cactacaatg attatcaatg agagaaacag aagatccaac attggcaatt 5160
gtatggaggc tttgtttcaa ggaccactcc agtataaaga cttgaaaatt gacatcaaga 5220
cgagtccccc tcctgaatgt atcaatgact tgctccaagc agttgactcc caggaggtga 5280
gagattactg tgagaagaag ggttggatag ttaacatcac cagccaggtt caaacagaaa 5340
ggaacatcaa cagggcaatg acaattctac aagcggtgac aaccttcgcc gcagtggctg 5400
gagttgtcta tgtcatgtat aaactgtttg ctggacacca gggagcatac actggtttac 5460
caaacaaaaa acccaacgtg cccaccattc ggacagcaaa ggtacaagga ccagggttcg 5520
attacgcagt ggctatggct aaaagaaaca ttgttacagc aactactagc aagggagagt 5580
tcactatgtt aggagtccac gacaacgtgg ctattttacc aacccacgct tcacctggtg 5640
aaagcattgt gatcgatggc aaagaagtgg agatcttgga tgccaaagcg ctcgaagatc 5700
aagcaggaac caatcttgaa atcactataa tcactctaaa gagaaatgaa aagttcagag 5760
acattagacc acatatacct actcaaatca ctgagacaaa tgatggggtc ttgatcgtga 5820
acactagcaa gtaccccaat atgtatgttc ctgtcggtgc tgtgactgaa cagggatatc 5880
taaatctcgg tgggcgccaa actgctcgta ctctaatgta caactttcca accagagcag 5940
gacagtgtgg tggagtcatc acatgtactg ggaaagtcat cgggatgcat gttggtggga 6000
acggttcaca cgggtttgca gcggccctga agcgatcata cttcactcag agtcaaggtg 6060
aaatccagtg gatgagacct tcgaaggaag tgggatatcc aatcataaat gccccgtcca 6120
aaaccaagct tgaacccagt gctttccact atgtgtttga aggggtgaag gaaccagcag 6180
tcctcactaa aaacgatccc aggcttaaga cagactttga ggaggcaatt ttctccaagt 6240
acgtgggtaa caaaattact gaagtggatg agtacatgaa agaggcagta gaccactatg 6300
ctggccagct catgtcacta gacatcaaca tagaacaaat gtgcttggag gatgccatgt 6360
atggcactga tggtctagaa gcacttgatt tgtccaccag tgctggctac ccttatgtag 6420
caatgggaaa gaagaagaga gacatcttga acaaacaaac cagagacact aaggaaatgc 6480
aaaaactgct cgacacatat ggaatcaacc tcccactggt gacttatgta aaggatgaac 6540
ttagatccaa aacaaaggtt gagcagggga aatccagatt aattgaagct tctagtttga 6600
atgactcagt ggcaatgaga atggcttttg ggaacctata tgctgctttt cacaaaaacc 6660
caggagtgat aacaggttca gcagtggggt gcgatccaga tttgttttgg agcaaaattc 6720
cggtattgat ggaagagaag ctgtttgctt ttgactacac agggtatgat gcatctctca 6780
gccctgcttg gttcgaggca ctaaagatgg tgcttgagaa aatcggattc ggagacagag 6840
ttgactacat cgactaccta aaccactcac accacctgta caagaataaa acatactgtg 6900
tcaagggcgg tatgccatct ggctgctcag gcacttcaat ttttaactca atgattaaca 6960
acttgattat caggacactc ttactgaaaa cctacaaggg catagattta gaccacctaa 7020
aaatgattgc ctatggtgat gatgtaattg cttcctaccc ccatgaagtt gacgctagtc 7080
tcctagccca atcaggaaaa gactatggac taactatgac tccagctgac aaatcagcta 7140
catttgaaac agtcacatgg gagaatgtaa cattcttgaa gagattcttc agggcagacg 7200
agaaataccc atttcttatt catccagtaa tgccaatgaa ggaaattcat gaatcaatta 7260
gatggactaa agatcctagg aacactcagg atcacgttcg ctctctgtgc cttttagctt 7320
ggcacaatgg cgaagaagaa tataacaaat tcctagctaa aatcaggagt gtgccaattg 7380
gaagagcttt attgctccca gagtactcaa cattgtaccg ccgttggctt gactcatttt 7440
agtaacccta cctcagtcga attggattgg gtcatactgt tgtaggggta aatttttctt 7500

-continued

```
taattcggag gaaaaaaaaa aaaaaaaaaa aaaaaaaaaa aaaaaaaaaa aaaaaaaaaa   7560

aaaaaaaaaa                                                           7570


<210> SEQ ID NO 2
<211> LENGTH: 27
<212> TYPE: DNA
<213> ORGANISM: unknown
<220> FEATURE:
<223> OTHER INFORMATION: synthetic

<400> SEQUENCE: 2

caagttcaat aggagggggt acaaacc                                          27


<210> SEQ ID NO 3
<211> LENGTH: 26
<212> TYPE: DNA
<213> ORGANISM: unknown
<220> FEATURE:
<223> OTHER INFORMATION: synthetic

<400> SEQUENCE: 3

ctggtttgta ccccctccta ttgaac                                           26
```

ATTENUATED POLIOVIRUS

CROSS REFERENCE TO RELATED APPLICATIONS

This application claims priority to U.S. Application No. 61/036,925 filed Mar. 14, 2008, which is incorporated herein by reference in its entirety.

FEDERAL FUNDING

This invention was produced in part using funds obtained through NIAID Grants A139485 and A115122. The federal government has certain rights in this invention.

FIELD OF THE INVENTION

The present invention relates to novel attenuated polioviruses. The attenuated polioviruses are effective in oncolytic treatment and cure of human solid tumors, especially neuroblastoma.

BACKGROUND OF THE INVENTION

Neuroblastoma is one of the most common solid tumors in children (Katzenstein, 1998). Available treatment is of limited utility for high-risk neuroblastoma and prognosis is therefore poor (Weinstein, 2003). Currently, children with high-risk neuroblastoma are treated with radiotherapy, dose-intensive cycles of multi-drug chemotherapy or, if patients responded poorly, with myeloablative dose of chemotherapy supported by stem cell rescue. Despite an aggressive treatment strategy, disease relapse occurs frequently and both short- and long-term toxicities, including treatment-related acute myeloid leukemia, occur in a significant percentage of disease survivors (Kushner, 1998) (Matthay, 1999). The high incidence of resistance of advanced stage neuroblastoma to conventional therapies has prompted investigators to search for novel therapeutic approaches.

Replication-competent viruses that replicate in tumor cells and lyticly kill them with limited side effects have been reported to have great potential in anti-tumor therapy (Ring, 2002; Thorne, 2005; Young, 2006; Parato, 2005). It has been suggested that antigen-presenting cells might internalize antigen released from virus infected tumor cells, leading to specific peptide presentation and generation of cytotoxic T lymphocyte (CTL), which, in turn, may facilitate tumor killing (Porosnicu, 2003; Berwin, 2001).

Poliovirus has recently been added to the list of viruses that hold promise as possible agents in tumor therapy (Gromeier, 2000; Ochiai, 2006). A non-enveloped, plus-stranded enterovirus of the Picornaviridae family, poliovirus replicates in the gastrointestinal tract causing little, if any, clinical symptoms. Rarely (at a rate of $10^{-2}$ to $10^{-3}$), the virus invades the central nervous system (CNS) where it targets predominantly motor neurons, thereby causing paralysis and even death (poliomyelitis). Poliovirus occurs in three serotypes all of which are defined in their amino acid sequences that specify the antigenic properties. That is, poliovirus type 1 has a capsid specifying serotype 1 antigenic sites.

Generally, poliovirus replicates efficiently in nearly all tumor cell lines tested, which has led to the suggestion that it may be suitable for the treatment of different cancers. However, the possibility that poliovirus can cause poliomyelitis calls for significant neuro-attenuation to avoid collateral neurological complications in cancer treatment. Additionally, there has been concern that the high coverage of anti-polio vaccination in early childhood in the U.S. and other countries may interfere with the application of poliovirus in tumor therapy.

Pathogenesis of poliovirus and of other neurotropic viruses can be controlled by translation (Gromeier, 1996; Gromeier, 2000; Mohr, 2005). In poliovirus, an exchange of the internal ribosome entry site (IRES) within the 5'-NTR with its counterpart from human rhinovirus type 2 (HRV2), another picornavirus, yielded viruses (called PV1(RIPO)) that are highly attenuated in CD155 tg mice (Gromeier, 1996; Gromeier, 1999) yet replicate efficiently and lytically in cell lines derived from solid glioma and breast cancer (Gromeier, 1996; Gromeier, 2000; Ochiai, 2004; Ochiai, 2006). However, PV1 (RIPO) and PVS(RIPO), a derivative of PV1(RIPO), grow poorly in neuroblastoma cells (Gromeier, 1996; Gromeier, 2000).

With the exception of Raji cells, a Burkett's lymphoma cell line harboring a transcriptionally inactive CD155 gene (Solecki, 1997), wild type poliovirus kills all human tumor cells tested including neuroblastoma cell lines established from patients (Toyoda, 2004). Using the nude mice model, tumors of human origin can be successfully treated with neuroattenuated poliovirus strains, that is with PV(RIPO) derivatives (Gromeier, 2000), or with the Sabin vaccine strains (Toyoda, 2004). However, the lack of a possible immune response to the oncolytic agents mitigates the importance of the results. PVS(RIPO) is, in fact, under consideration for brain tumor therapy (Gromeier, 2000; Ochiai, 2006; Cello, 2008). However, as noted above, PVS(RIPO) replicates very poorly in human neuroblastoma cells, which disqualifies it from consideration in neuroblastoma therapy.

The whole genome synthesis of poliovirus (Cello, 2002) has produced, as by-product, the surprising observation that a point mutation ($A_{103}G$) in a region between the cloverleaf and IRES, henceforth called "spacer region", in the 5'-NTR (FIG. 1A) attenuated poliovirus neurovirulence 10,000 fold in CD155 tg mice (De Jesus, 2005). The $A_{103}G$ variant of poliovirus, named GG PV1(M), expresses a good replication phenotype in and kills human neuroblastoma cells (SK-N-MC) at 37° C. (De Jesus, 2005). This growth property of GG PV1 (M) is different from that of PV(RIPO). However, GG PV1 (M) is not useful in tumor therapy because the attenuating mutation $A_{103}G$ in the spacer region was unstable upon replication, and direct revertant variants rapidly emerge whose neurovirulence matches that of wt PV1(M) (De Jesus, 2005).

Novel therapeutic strategies are essential to improve the prognosis of patients with high-risk neuroblastoma. Neuroblastoma therapy with a poliovirus derivative may produce less toxicity often associated with chemotherapy and radiotherapy and complications such as second solid neoplasm, cardiopulmonary sequelae, renal dysfunction and endocrine consequences may not occur. The invention of a novel attenuated and stable poliovirus that will be effective in oncolytic treatment and cure of neuroblastoma is highly desirable.

SUMMARY OF THE INVENTION

The invention provides a stably attenuated poliovirus with enhanced replication properties in human tumor cells, which is effective in treating human solid tumors, particularly neuroblastoma.

In one embodiment, the invention provides a stably attenuated recombinant poliovirus containing a single active cre regulatory element, said cre element located in the spacer region of the 5'-NTR between the cloverleaf and internal ribosome entry site (IRES), so as to produce a stable attenuated phenotype. In an embodiment of the invention, the cre element is inserted into the spacer region at nucleotide 102/103. In such a virus, the native cre element, which is in the 2C coding region of the poliovirus genome is inactivated or deleted.

In another embodiment of the invention, the stably attenuated poliovirus comprises a point mutation which enhances replication properties of the virus. In a particular embodiment, the recombinant poliovirus comprises an $A_{133}G$ transition in domain II of the IRES, which enhances replication properties of the poliovirus in CD155 tg mice.

The invention also provides a composition comprising a stably attenuated recombinant poliovirus of the invention and a pharmaceutically acceptable carrier. In various embodiments the invention may be such a composition wherein the composition is infusible, injectable, the pharmaceutically acceptable carrier is a physiological salt solution, the physiological salt solution is HANKS balanced salt solution, or anti-poliovirus antibodies are systematically administered along with the said composition.

The invention also provides a therapeutic method of treating a solid tumor in a subject comprising administering at the tumor site a therapeutically effective amount of a composition comprising a stably attenuated recombinant poliovirus of the invention, containing a single active cre regulatory element, said cre element located in the spacer region of the 5'-NTR between the cloverleaf and internal ribosome entry site (IRES), wherein the recombinant poliovirus infects and causes lysis of the tumor cells. In an embodiment of the invention, the composition is administered by intratumoral injection. In another embodiment of the invention, the threapeutic method further inhibits tumor recurrence. According to the invention, the recombinant poliovirus used in the therapeutic method further comprises one or more nucleotide substitutions which provide for enhanced replication properties, such as an $A_{133}G$ transition in domain II of the internal ribosome entry site (IRES).

In an embodiment of the invention, the therapeutic method involves administration of the recombinant poliovirus of the invention after anti-poliovirus immunity has been elicited in the subject by immunization. In another embodiment of the invention, wherein the subject is immunocompromised, temporary immunity is conferred by passive immunization with anti-poliovirus antibodies. According to the invention, anti-poliovirus immunity is matched to the serotype of the oncolytic poliovirus that is administered at the site of the tumor.

According to the invention, a variety of solid tumors are treated. In one embodiment, the tumor is a neuroblastoma. In other embodiments, the tumor to be treated is one of the breast, colon, lung, epithelial lining of the gastrointestinal, upper respiratory tract, genito-urinary tracts, liver, prostate, adrenal gland, pancreas, abdominal cavity, or brain.

The invention further provides a method of producing a recombinant poliovirus with the cre regulatory element in the spacer region between the cloverleaf and IRES in the 5'-NTR so as to produce a stable attenuated phenotype, characterized by the following steps: a) inserting a cre regulatory element into the spacer region between the cloverleaf and the internal ribosome entry site (IRES) in the 5'-NTR of a poliovirus genome; b) inactivating the native cre element in the 2C coding region of the poliovirus genome; c) inserting an $A_{133}G$ transition in domain II of the internal ribosome entry site; d) introducing the poliovirus genome into an appropriate host cell, and e) growing the virus in the host cell.

In a further embodiment, the invention further comprises selecting a point mutation that enhances replication of the recombinant poliovirus by repeatedly passaging the recombinant poliovirus in the host cell. In other embodiments of the invention, the host cell is a HeLa cell or a Neuro-$2a^{CD155}$ cell.

In another embodiment, the method of the invention includes a kit comprising a recombination poliovirus according to the invention and a pharmaceutically acceptable carrier, an applicator, and an instructional material for the use thereof.

DETAILED DESCRIPTION

Figure 1:
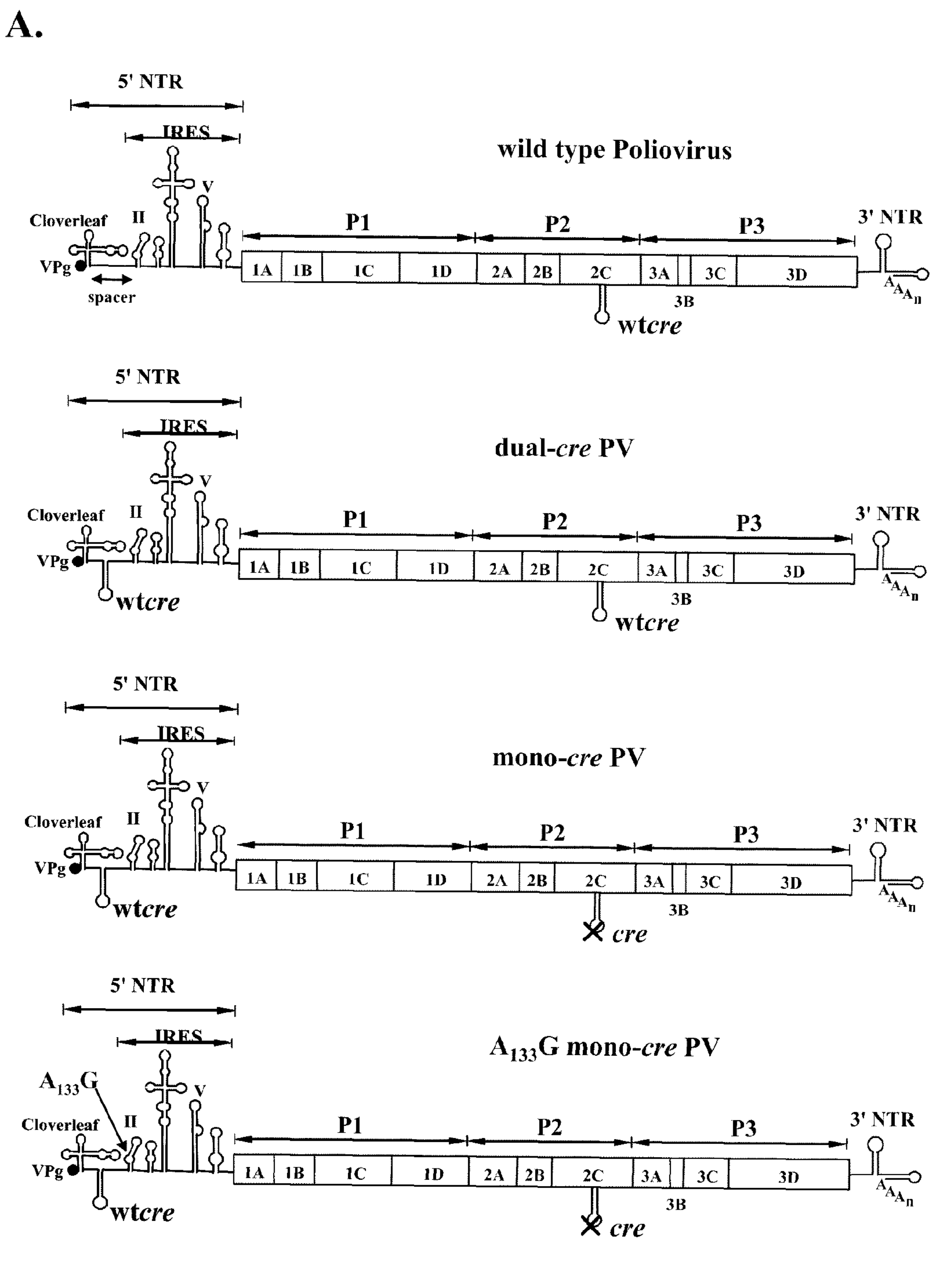
FIG. 1. Genomic organization of poliovirus and one-step growth curve for mono-crePV and dual-crePV. A, Structure of the PV1(M), dual-crePV, mono-crePV and $A_{133}$Gmono-crePV genome. The single-stranded RNA is covalently linked to the viral-encoded protein VPg at the 5' end of the non-translated region (5'-NTR). The 5'-NTR consists of two cis-acting domains, the cloverleaf and the internal ribosomal entry site (IRES), which are separated by a spacer region. The IRES controls translation of the polyprotein (open box), consisting of structural (P1) region and nonstructural regions (P2 and P3), specifying the replication proteins. Within the $2C^{ATPase}$ coding region, the cis replication element (cre) is indicated. The 3'-NTR contains a heteropolymeric region and is polyadenylylated. RNA replication requires all three structural elements, cloverleaf, cre and the 3'-NTR. The duplicated cre was inserted into the spacer between cloverleaf and IRES (dual-crePV). The native cre in $2C^{ATPase}$ was inactivated by mutation as indicated by an X (mono-crePV). A point mutation ($A_{133}G$) was engineered into domain II of the 5'-NTR in mono-crePV ($A_{133}$Gmono-crePV). Wt, wild type. B, One-step growth curves for mono-crePV and dual-crePV in HeLa cells (upper panel) and SK-N-MC cells (lower panel). Cells were infected at an MOI of 10 and incubated at 37° C. or 39.5° C. The virus titer was determined by plaque assay on monolayers of HeLa cells.

The invention provides highly attenuated polioviruses that are suitable for the treatment or amelioration of human solid tumors, such as neuroblastoma in children. The invention also provides an immunocompetent animal model that allows investigation of the oncolytic capacity of neuro-attenuated polioviruses for the treatment of neuroblastoma in the presence of high titers of poliovirus neutralizing antibodies.

A stable attenuated phenotype can be generated if the spacer region between cloverleaf and IRES of the poliovirus genome is interrupted by an essential RNA replication element that the virus cannot afford to delete. Such an element is the cre, a stem-loop structure mapping to the coding region of viral protein $2C^{ATPase}$ in native poliovirus (FIG. 1A) (Paul, 2002). According to the invention, a single active cre element is provided in the 5'-NTR of the poliovirus genome at a position which results in viral attenuation, and wherein any mutation of the element that would revert the attenuation results in inactivation of the cre element such that the poliovirus becomes non-viable. According to the invention, an active cre element is inserted into the spacer region of the 5'-NTR between the cloverleaf and the internal ribosome entry site (IRES). In a particular embodiment, the cre element is inserted into the spacer region at nucleotides 102/103.

It will be appreciated that the stability of attenuation depends on the cre element located in the 5'-NTR being the only active cre element. Accordingly, the native cre element, located in the 2C coding region of the poliovirus genome, is inactivated. Typically, the sequence of the native cre element, which is in a coding region, is mutated to inactivate the cre element, but not alter the amino acids encoded by the nucleotides of the cre element. However, mutations that result in conservative amino acid substitutions are allowable. A conservative amino acid substitution is a substitution with an amino acids having generally similar properties (e.g., acidic, basic, aromatic, size, positively or negatively charged, polarity, non-polarity) such that the substitutions do not substantially alter peptide, polypeptide or protein characteristics (e.g., charge, isoelectric point, affinity, avidity, conformation, and solubility) or activity. Typical substitutions that may be performed for such conservative amino acid substitution may be among the groups of amino acids as follows:

glycine (G), alanine (A), valine (V), leucine (L) and isoleucine (I);
aspartic acid (D) and glutamic acid (E);
alanine (A), serine (S) and threonine (T);
histidine (H), lysine (K) and arginine (R):
asparagine (N) and glutamine (Q);
phenylalanine (F), tyrosine (Y) and tryptophan (W)

The stably attenuated virus is administered directly to tumor tissue, for example, by injection. In an embodiment of the invention, the virus is modified to enhance replication properties in tumor tissue, while retaining an attenuated phenotype. A non-limiting example of a genome of such a virus is provided by $A_{133}$Gmono-crePV (SEQ ID NO:1), in which an A to G transition mutation (relative to PV Mahoney) is present at nucleotide position 133 (i.e., corresponding to nucleotide position 133 of PV Mahoney), and provides for enhanced replication in a human tumor model. (e.g., CD155 transgenic mice). In various human solid tumors, the same or different mutation may enhance poliovirus replication. According to the invention, one way such mutations can be obtained is by viral passage and testing for enhancement of poliovirus replication properties. Another way is by in vitro mutagenesis.

The invention further provides construction of fully immunocompetent mice (CD155 tgA/J mice) that express CD155 and accept Neuro2a$^{CD155}$ cells for the formation of lethal neuroblastoma. Neuroblastoma bearing CD155 tgA/J mice that were fully protected against lethal doses of wild type PV1(M) can be cured by intra-tumoral administration of a variant of mono crePV ($A_{133}$Gmono-crePV). Remarkably, the tumor bearing mice, which were cured through treatment with $A_{133}$Gmono-crePV, resist attempts to reestablish neuroblastoma with Neuro-2a$^{CD155}$ cells. These data indicate that the invention is useful for viral oncolytic therapy against human solid tumors, such as high-risk neuroblastoma in the general pediatric population.

According to the invention, neurovirulent poliovirus isolates can be stably attenuated, and replicative properties enhanced. Such neurovirulent poliovirus can be naturally occurring isolates, or derivatives thereof. Poliovirus type 1 (Mahoney) (PV1(M)) is exemplified herein. Other non-limiting examples of neurovirulent poliovirus include P3/Leon/37 (from which the attenuated Sabin vaccine is derived) and neurovirulent derivatives of those P3/Leon/37 and Mahoney. For example, non-attenuating mutations present in attenuated poliovirus (such as Sabin) have been distinguished in the art from those that cause attenuation. Further examples are poliovirus isolates from individuals who chronically excrete neurovirulent poliovirus of vaccine-origin.

According to the invention, a cre element is inserted into the 5'-NTR between the cloverleaf and the internal ribosome entry site (IRES) such that an attenuated virus results. As exemplified herein, a cre element is inserted into an NheI site created at nucleotide 102/103 in the 5'-NTR of PV1(M) (see SEQ ID NO:1), but need not be so precisely located. Attenuation may be determined, for example, by plaque assay or other techniques that are known in the art for measuring virus replication. cre element have been identified in the genomes of several picornaviruses, including poliovirus types 1 and 3, human rhinovirus (e.g., HRV2 and HRV14), cardioviruses. The cre elements are predicted to form hairpin structures with a conserved sequence of about 14 nucleotides at the loop portion of the hairpin. In an embodiment of the invention, the cre element is from the poliovirus type 1 designated PV1(M).

As exemplified herein, the replicative properties of an attenuated poliovirus can be enhanced by passage, in vitro, and in vivo. As demonstrated herein, mutations occur in attenuated viruses of the invention during passage, but are not observed to occur in the cre element engineered into the 5'-NTR. Accordingly, viral attenuation is not overcome. Rather, the mutations provide for enhancement of replication properties that are beneficial for oncolytic treatment of tumors. Further, such mutations are readily obtainable. Accordingly, the invention provides a stably attenuated poliovirus containing a single active cre regulatory element in the 5'-NTR, and a mutation that enhances replication. By enhanced, it is meant that viral replication is increased relative to a "wild type" neurovirulant poliovirus such as PV1(M) that contains the same cre element modifications in the 5'-NTR. In one embodiment of the invention (i.e. SEQ ID NO:1), the mutation that enhances replication properties is an A to G transition at nucleotide 133 in domain II of the internal ribosome entry site (IRES).

Recombinant polioviruses can be synthesized by well-known recombinant DNA techniques. Any standard manual on DNA technology provides detailed protocols to produce the recombinant polioviruses of the invention. (Sambrook, Fritsch and Maniatis, Molecular Cloning, Cold Spring Harbor Laboratory Press, NY (1989). Exemplary detailed cloning instructions for the construction of such recombinant viruses are provided below and in the Examples.

The recombinant polioviruses of the invention are oncolytic and useful for treatment of solid tumors. As exemplified herein using a human neuroblastoma model, oncolytic poliovirus of the invention provides a powerful tool for treatment of neuroblastoma and solid tumors more generally, and can further induce host immune defenses that are effective against tumor recurrences. Initially, prior to oncolytic treatment of a subject, in order to provide or boost protective immunity against poliovirus harmful infection of neural tissue, it is preferable to immunize a subject. Immunization can be by any method known in the art, such as by injection or oral administration. In the case of an immunocompromized subject, it may be preferable to passively immunized by injection of anti-poliovirus antibodies. Passive immunization can be by any method known in the art, though intravenous administration is usually preferred. As exemplified herein, in order to provide protective immunity against harmful poliovirus infection, CD155 tgA/J mice were immunized by intraperitoneal injection of mono-crePV ($1\times10^8$ pfu) three times with intervals of one week, and neutralizing antibody was titered.

Once a sufficient antibody titer is established, an oncolytic poliovirus of the invention is administered. Although the therapeutic oncolytic polioviruses can be delivered by various routes, including intravenously, the preferred mode of administration is directly to the tumor site, for example, by injection into the tumor.

In a neuroblastoma model demonstrated herein, Neuro-$2a^{CD155}$ cells ($1\times10^7$) were subcutaneously implanted in the right flank of the immunized CD155 tgA/J mice described above. According to the invention, when the subcutaneous tumor volumes were approximately 170 $mm^3$ (approximately 7-12 days after implantation), mice were inoculated intratumorally with $A_{133}$Gmono-crePV or PBS, respectively. By day 8, tumors had grown in PBS treated mice to >17 mm in diameter. In contrast, marked tumor regression was observed in all of the $A_{133}$Gmono-crePV treated mice, and most of the $A_{133}$Gmono-crePV treated mice showed no evidence of recurrent tumors after 6 months. In the few mice in which tumors recurred, CD155 expression was very low compared to the non-recurrent tumors. Further, when the surviving mice were rechallenged with Neuro-$2a^{CD155}$ cells at a different location (the opposite flank), no tumors developed at the site of inoculation or elsewhere.

Thus, the invention provides not only a method of treating a tumor in a subject, by administering a stably attenuated recombinant poliovirus of the invention to the subject, such that tumor cells are lysed, but also a method of inhibiting tumor recurrence. In an embodiment of the invention, an immune response is elicited when a tumor is treated, such that recurring tumors are inhibited. This "prophylactic" anti-tumor response can be confirmed by collecting immune serum and/or immune cells from the subject and detecting immune activity against the subjects own tumor cells in an in vitro assay. As exemplified herein in test animals, immune cells conferring anti-tumor protection can be adoptively transferred.

The recombinant polioviruses of this invention are useful in prophylactic and therapeutic compositions for treating malignant tumors in various organs, such as breast, colon, bronchial passage, epithelial lining of the gastrointestinal, upper respiratory and genito-urinary tracts, liver, prostate, adrenal glands, pancreas, abdominal cavity, and the brain.

Pharmaceutical compositions of the invention comprise a therapeutically effective amount of one or more recombinant polioviruses according to this invention, and a pharmaceutically acceptable carrier. By "therapeutically effective amount" is meant an amount capable of causing lysis of the cancer cells and/or tumor necrosis. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the poliovirus chimeras.

The compositions of this invention may be in a variety of forms. These include, for example, liquid dosage forms, such as liquid solutions, dispersions or suspensions, injectable and infusible solutions. The preferred form depends on the intended mode of administration and prophylactic or therapeutic application. The preferred compositions are in the form of injectable or infusible solutions.

Therapeutic oncolytic polioviruses can be delivered intravenously or intraneoplastically (directly into the primary tumor) or by any other route. The preferred mode of administration is directly to the tumor site. For all forms of delivery, the recombinant virus is most preferably formulated in a physiological salt solution: e.g. HANKS balanced salt solution (composition: 1.3 mM $CaCl_2$ (anhyd.), 5.0 mM KCl, 0.3 mM $KH_2$ $PO_4$, 0.5 mM $MgCl_26H_2O$, 0.4 mM $MgSO_47H_2O$, 138 mM NaCl, 4.0 mM $NaHCO_3$, 0.3 mM $Na_2$ $HPO_4$, 5.6 mM D-Glucose). The inoculum of virus applied for therapeutic purposes can be administered in an exceedingly small volume ranging between 1-10 μl. Recombinant polioviruses stored in a physiological salt solution of the composition detailed above can be stored at −80° C. for many years with minimal loss of activity. Short term storage should be at 4° C. At this temperature virus solutions can be stored for at least one year with minimal loss of activity.

It will be apparent to those of skill in the art that the therapeutically effective amount of recombinant polioviruses of this invention will depend upon the administration schedule, the unit dose of recombinant polioviruses administered, whether the recombinant polioviruses is administered in combination with other therapeutic agents, the status and health of the patient.

The therapeutically effective amounts of oncolytic recombinant virus can be determined empirically and depend on the maximal amount of the recombinant virus that can be administered safely, and the minimal amount of the recombinant virus that produces efficient oncolysis. The dose may be adjusted in accordance with the particular recombinant poliovirus contemplated, the sized of the tumor, and the route of administration desired.

The mechanism by which oncolysis takes place is by the ability of these recombinant polioviruses to replicate in the cancer cells at a rate which causes the destruction of cells. The recombinant polioviruses of the present invention do not affect normal cellular processes and are thus not expected to be toxic to normal cells of an immunized subject. Therefore, it would appear that there is no upper limit to the dose level which can be administered. Thus, to produce the same oncolytic effect achieved through intraneoplastic inoculation of virus by the intravenous route, significantly higher amounts of virus should be and could be administered. However, in an abundance of caution, the appropriate dose level should be the minimum amount which would achieve the oncolytic effect.

Therapeutic inoculations of oncolytic polioviruses can be given repeatedly, depending upon the effect of the initial treatment regimen. Since poliovirus exists in three antigenically distinct serotypes, candidate oncolytic polioviruses will be available as three different serotypes. Any one of the three serotypes can be used provided the patient is protected to the serotype by adequate immunization. The host's immune response to a particular poliovirus can be easily determined serologically.

For that purpose, serological data on the status of immunity against any given poliovirus can be used to make an informed decision on which variant of the oncolytic poliovirus to be used. For example, if a high titer against poliovirus serotype 1 is evident through serological analysis of a candidate patient for treatment with an oncolytic non-pathogenic polioviruses, a serotype 1 oncolytic virus can be used for tumor treatment.

The pharmaceutical compositions of this invention may include or be combined with other therapeutics for treatment of prophylaxis of malignant tumors. For example, the recombinant polioviruses of this invention may be used in combination with surgery, radiation therapy and/or chemotherapy. Furthermore, one or more recombinant polioviruses may be used in combination with two or more of the foregoing therapeutic procedures. Such combination therapies may advantageously utilize lower dosages of the administered therapeutic agents, thus avoiding possible toxicities or adverse effects associated with the various monotherapies.

The method of the invention includes a kit for administering to a cell a composition comprising a recombinant poliovirus of the invention and a pharmaceutically acceptable carrier. The kit comprises a recombinant poliovirus as disclosed herein. The kit can further comprise a pharmaceutically acceptable carrier, an applicator, such as a syringe, and an instructional material for the use thereof. The instructions can provide any information that is useful for directing the administration of the recombinant poliovirus for the treatment of solid tumors, such as treatment of neuroblastoma, or for propagating the virus. In an embodiment of the invention, the kit provides a mammalian cell, such as a human cell or a transgenic mouse cell the expressed CD155.

The present invention is not to be limited in scope by the specific embodiments described herein which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the claims. Throughout this application, various publications are referenced. The disclosures of these publications in the entireties are hereby incorporated by reference into this application in order to more fully describe the state of the art to those skilled therein as of the date of the invention described and claimed herein.

EXAMPLE 1

Construction of Plasmids and DNA Manipulation

The neurovirulent poliovirus type 1 (Mahoney) was the strain used in the laboratory (Cello, 2002). The mouse neuroblastoma cell line stably expressing CD155α (Neuro-$2a^{CD55}$) has been described (Mueller, 2003). Neuro-$2a^{CD155}$ cells, which are susceptible to poliovirus infection, were maintained in Dulbecco's modified Eagle's medium containing 1% penicillin/streptomycin and 10% fetal bovine serum. HeLa cells and human neuroblastoma cell lines SK-N-MC, SK-N-SH and SH-SY5Y were obtained from the American Type Culture Collection (Manassas, Va.) and were maintained according to the manufacture's specification.

The poliovirus cDNA sequence was that used by Cello et al. (2002) for cDNA synthesis (plasmid pT7PVM) (van der Werf, 1986). "pT7PVM cre($2C^{ATPase}$) mutant" is a full-length poliovirus cDNA clone in which the native cre element in the $2C^{ATPase}$ coding region was inactivated by introducing three mutations at nt 4462 (G to A), 4465 (C to U), and 4472 (A to C) (Yin, 2003; Paul, 2003; Rieder, 2000). Dual-cre PV is a derivative of pT7PVM carrying two active cre elements; one at nt 102/103 of the 5'-NTR at which a new Nhe I restriction site was created. The second cre element is in the $2C^{ATPase}$ coding region (FIG. 1A). Mono-crePV has the active cre in the spacer region whereas the native cre in the $2C^{ATPase}$ coding region has been inactivated (FIG. 1A). To construct $A_{133}$Gmono-crePV, which has a single $A_{133}$G mutation in the 5'-NTR, site-directed mutagenesis was performed with the QuickChange mutagenesis kit from Stratagene using primers (5'-CAAGTTCAATAGGAGGGGGTACAAACC-3'; SEQ ID NO:2) and (5'-CTGGTTTGTACCCCCTCCTATTGAAC-3'; SEQ ID NO:3). Mutations and final constructs were verified through sequencing using the ABI Prism DNA Sequencing kit.

FIG. 1A shows the structure of the $A_{133}$Gmono-crePV genome: The single-stranded RNA is covalently linked to the viral-encoded protein VPg at the 5' end of the non-translated region (5'-NTR). The 5'-NTR consists of two cis-acting domains, the cloverleaf and the internal ribosomal entry site (IRES), which are separated by a spacer region. The IRES controls translation of the polyprotein (open box), consisting of structural (P1) region and nonstructural regions (P2 and P3), specifying the replication proteins. Within the $2C^{ATPase}$ coding region, the cis replication element (cre) is indicated. The 3'-NTR contains a heteropolymeric region and is polyadenylylated. RNA replication requires all three structural elements, cloverleaf, cre and the 3'-NTR. The native cre in $2C^{ATPase}$ was inactivated by mutation as indicated by an X (mono-crePV). A point mutation ($A_{133}$G) was engineered into domain II of the 5'-NTR in mono-crePV ($A_{133}$Gmono-crePV). Wt, wild type.

EXAMPLE 2

In vitro Transcription, Transfection and One-step Growth Curves

All plasmids were linearized with DraI. RNAs were synthesized with phage T7 RNA polymerase, and the RNA transcripts were transfected into HeLa cell monolayers by the DEAE-dextran method as described previously (van der Werf, 1986). The incubation time was up to 2 days and virus titers were determined by a plaque assay (Pincus, 1986). One-step growth curves in HeLa, Neuro-$2a^{CD155}$, SK-N-MC, SK-N-SH and SH-SY5Y were carried out as follows. Cell monolayers ($1\times10^6$ cells) were infected at a multiplicity of infection (MOI) of 10. The plates were incubated at 37° C. or at 39.5° C., as indicated, and the cells were harvested at 0, 2, 4, 6, 8, 12 and 24 h post infection. The plates were subjected to three consecutive freeze-thaw cycles, and the viral titers of the supernatants were determined by plaque assay on HeLa cell monolayers, as describe before (Pincus, 1986).

Results are shown in FIG. 1B. The insertion of the duplicated cre element into the 102/103 locus does not interfere with virus replication in HeLa cells. Moreover, inactivation of the endogenous cre by three point mutations yielded a variant replicating also with a wt phenotype in HeLa cells. Although both mono-crePV and dual-crePV replicated in human neuroblastoma SK-N-MC cells at 37° C. they are strongly restricted at 39.5° C. a phenotype reminiscent of GG PV1(M).

EXAMPLE 3

Neurovirulence Assays

Groups of four CD155 tg mice or CD155 tgA/J mice (equal number of male and females) were inoculated with any given amount of virus ranging from $10^1$ to $10^7$ plaque-forming unit (pfu) (30 μl/mouse) intracerebrally or intramuscularly with mono-crePV, $A_{133}$Gmono-crePV, dual-crePV and wt PV1 (M). Mice were examined daily for 21 days post-inoculation for paralysis and/or death. The virus titer that induced paralysis or death in 50% of the mice ($PLD_{50}$) was calculated by the method of Reed and Muench (Reed, 1938).

EXAMPLE 4

Characterization of Novel Neuroattenuated Poliovirus Strains

A single point mutation in the 5'-NTR of the poliovirus genome neuroattenuates poliovirus in CD155 tg mice, but the mutant replicates in and kills neuroblastoma cells. However, revertants rapidly emerge whose neurovirulence matches that of wild type PV1 (M). The GG dinucleotide mutation of GG PV1 (M) (nt 102/103) maps to a region in the poliovirus genome (the spacer region) that previously had not been implicated in poliovirus pathogenesis. To genetically stabilize the attenuated phenotype of GG PV1(M), the invention provides poliovirus constructs in which the cre, an essential cis acting replication element mapping to the coding region of protein $2C^{ATPase}$ (FIG. 1A), was placed into the nt 102/103 locus. The insertion of the duplicated cre element into the 102/103 locus (dual-crePV; FIG. 1A) does not interfere with virus replication in and killing of HeLa cells (FIG. 1B) (Yin, 2003). Moreover, inactivation of the endogenous cre by three point mutations (mono-crePV; FIG. 1A) yielded a variant replicating also with a wt phenotype in HeLa cells (FIG. 1B) (Yin, 2003). Although both mono-crePV and dual-crePV replicated in human neuroblastoma SK-N-MC cells at 37° C. they are strongly restricted at 39.5° C. (FIG. 1B), a phenotype reminiscent of GG PV1(M) (De Jesus, 2005). Intracerebral injection of mono-crePV or dual-crePV into CD155 tg mice revealed a very strong attenuation phenotype (Table 1) and neurovirulent variants of mono-crePV have never been isolated from infected animals (data not shown).

TABLE 1

Neuropathogenicity of wt poliovirus PV(M), dual-crePV, mono-crePV, and $A_{133}$Gmono-crePV

| Virus | $PLD_{50}$ (pfu)* in PVR transgenic mice | $PLD_{50}$ (pfu)* in PVR transgenic A/J mice |
|---|---|---|
| wt PV1(M) | $10^{1.8}$ | $10^{2.0}$ |
| Dual-crePV | $>10^{7.0}$ | $>10^{7.0}$ |
| Mono-crePV | $>10^{7.0}$ | $>10^{7.0}$ |
| $A_{133}$Gmono-crePV | $10^{4.5}$ | $10^{4.8}$ |

*Defined as the amount of virus that causes paralysis or death in 50% of PVR transgenic mice or PVR transgenic A/J mice after i.c. inoculation

EXAMPLE 5

Immunocompetent CD155 tg A/J Mice

The transgenic mice that express human CD155 under its original promoter (ICR-CD155/Tg21) were kindly provided by Dr. A. Nomoto (Koike, 1991). The CD155 tg mice were kept in the homozygous state. A/J mice, which express the major histocompatibility complex (MHC) haplotype $H\text{-}2^a$, were purchased from the Jackson Laboratories. A/J mice carrying CD155 gene were obtained by outcrossing A/J mice with CD155 tg mice and called CD155 tgA/J mice. The CD155 tgA/J mice are heterozygous for CD155 and $H\text{-}2^a$. Mice were at least six weeks of age before use. All procedures involving experimental mice were conducted according to protocols approved by the institutional committees on animal welfare.

For testing mono-crePV as a candidate to treat solid tumors, such as anti neuroblastoma therapy, neuroblastoma tumors are generated in a mouse model susceptible to poliovirus. CD155 tg mice (strain ICR-CD155/Tg21) (Koike, 1991) were used as a mouse model since they are susceptible to poliovirus infection via the intracerebral, intraperitoneal, intramuscular, subcutaneous, and intravenous routes (Koike, 1991) and infected mice develop a paralytic disease resembling human poliomyelitis (Koike, 1991). The invention provides a cell line (Neuro-2a CD55) which is susceptible to poliovirus infection (Mueller, 2003). Neuro-2a$^{CD155}$ cells, however, cannot establish tumors in CD155 tg mice because the original Neuro-2a cell line was developed from a spontaneous tumor in A/J mice. In contrast to CD155 tg mice, A/J mice express the major histocompatibility complex (MHC) H-2' (data not shown). Accordingly, the CD155 gene was introduced into A/J mice via outcrossing and CD155 tgA/J mice were obtained that responded to poliovirus infection indistinguishably from CD155 tg mice. The $PLD_{50}$ value of CD155 tgA/J mice inoculated intracerebrally with wt PV1 (M) was nearly identical to that of CD155 tg mice (Table 1) and both mono-crePV and dual-crePV expressed the same striking attenuated phenotype in these new transgenic animals (Table 1). Importantly, subcutaneous injection of $1\times10^7$ Neuro-2a$^{CD155}$ cells into the hind flank of CD155 tgA/J mice established tumors in 80% of the animals. The tumors progressed to a mean tumor volume of 570.6 $mm^3$ after 2 weeks and all tumor-bearing mice were sacrificed when their tumors reached >17 mm in maximal diameter.

EXAMPLE 6

Serial Passages of Mono-crePV in Neuro-2a$^{CD155}$ Cells

The selection of mono-crePV variants capable of efficient replication in Neuro-2a$^{CD155}$ and SK-N-MC cells was carried out according to the following procedure: Neuro-2a$^{CD155}$ and SK-N-MC cells were infected with the mono-crePV at a MOI of 10 and incubated at 39.5° C. for 48 hours. Infected cells were then lysed by three freeze-thaw cycles and the supernatant fluid was harvested and clarified by low-speed centrifugation. Virus stock from each passage was obtained by growing the virus in HeLa at 37° C. After fifteen passages, RNA extracted from the viral cell lysate served as template for RT-PCR and purified PCR amplicons were used for sequencing reactions. Isolation of viral RNA, RT-PCR, purification of PCR products and sequencing were carried out as described previously (Cello, 2002).

EXAMPLE 5

Figure 2:
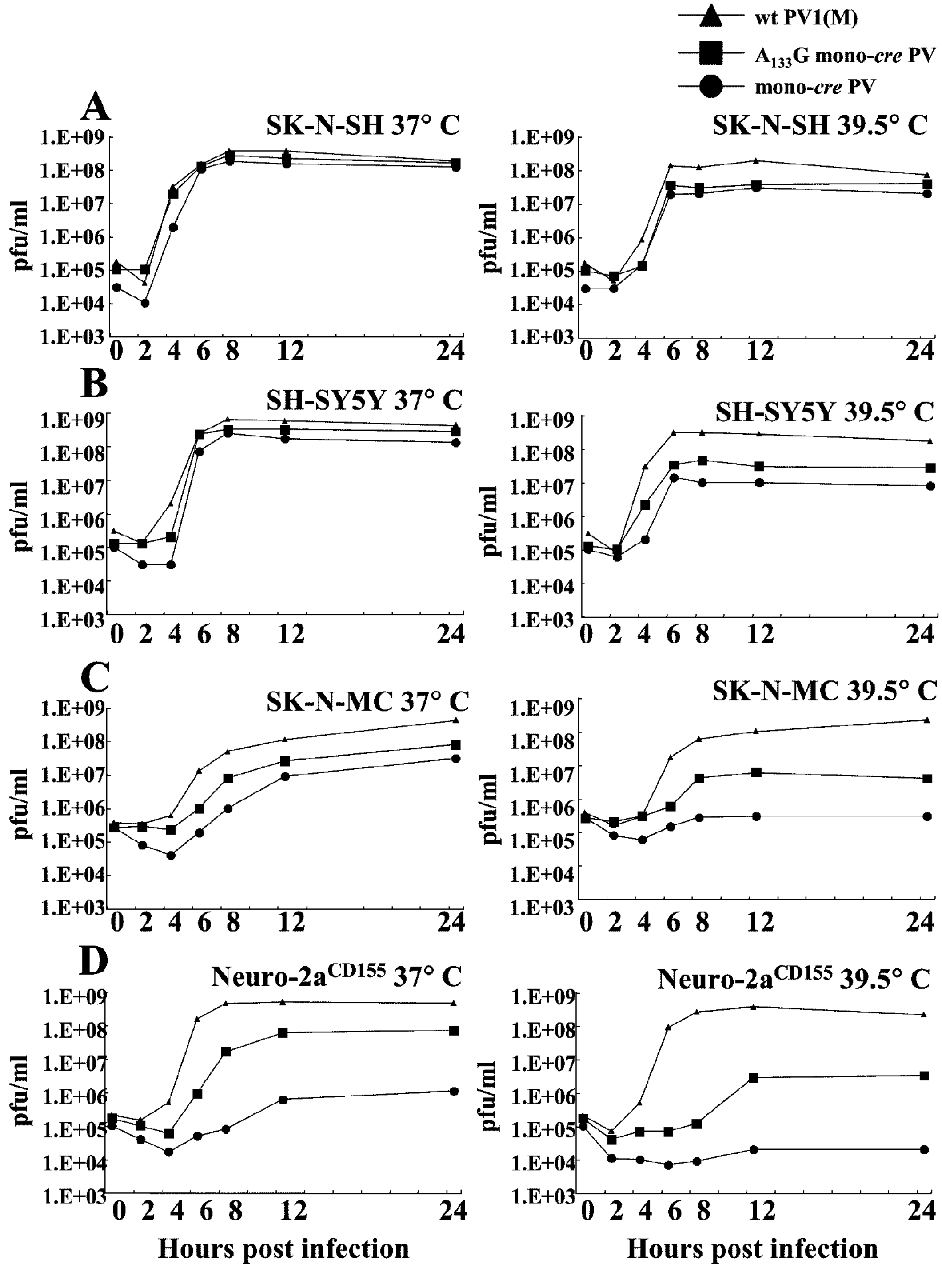
FIG. 2. One-step growth curves of polioviruses in different human and mouse neuroblastoma cells. Cells were infected as described in FIG. 1B with PV1(M) (closed triangle), mono-crePV (closed circle), and $A_{133}$Gmono-crePV (close square). A, human SK-N-SH at 37° C. and 39.5° C., B, human SH-SY5Y at 37° C. and 39.5° C., C, human SK-N-MC at 37° C. and 39.5° C., D, mouse Neuro-$2a^{CD155}$ at 37° C. and 39.5° C.

Oncolytic Effect on Tumor Grafts of Mono-crePV and Variants Adapted by Repeated Passage Treatment of four CD155-transgenic A/J mice bearing subcutaneous tumors with a dose of $1\times10^8$ pfu of mono-crePV did not lead to tumor regression (data not shown). It was observed that mono-crePV replicates poorly in mouse Neuro-2a CD55 cells (FIG. 2D). However, although none of the treated mice developed paralysis, virus recovered from tumors of these mice revealed what appeared to be adaptive mutations scattered over a wide range of the genome: $A_{133}G$, $C_{2575}A$, $A_{3719}C$, $C_{5584}G$, $A_{6427}G$, and $U_{6607}A$.

The selection of mono-crePV variants capable of efficient replication in Neuro-2a$^{CD155}$ and SK-N-MC cells was carried out according to the following procedure: Neuro-2a$^{CD155}$ and SK-N-MC cells were infected with the mono-crePV at a MOI of 10 and incubated at 39.5° C. for 48 hours. Infected cells were then lysed by three freeze-thaw cycles and the supernatant fluid was harvested and clarified by low-speed centrifugation. Virus stock from each passage was obtained by growing the virus in HeLa at 37° C. After fifteen passages, RNA extracted from the viral cell lysate served as template for RT-PCR and purified PCR amplicons were used for sequencing reactions. Isolation of viral RNA, RT-PCR, purification of PCR products and sequencing were carried out as described previously (Cello, 2002).

mono-crePV was passaged fifteen times on SK.N-MC or on Neuro-2a$^{CD155}$ cells and the total RNAs of putative variants after RT-PCR were sequences. The analyses showed that the cre element in the 5'-NTR was retained after passages in both cell lines. Seven mutations accumulated in variants after serial passage in SK-M-NC ($A_{133}G$, $A_{807}G$, $G_{1264}A$, $A_{3787}G$, $C_{5699}U$, $A_{6260}C$, and $U_{6261}G$) and five mutations ($G_{11}A$, $A_{133}G$, $A_{145}C$, $C_{2607}U$, and $G_{3543}C$) after serial passage in Neuro-2a CD55 cells. The $A_{133}G$ transversion was observed in both cell culture- and tumor-adapted mono-crePV, an observation suggesting that this mutation is responsible for the increased replication. Engineering just this $A_{133}G$ transition into mono-crePV yielded the variant $A_{133}$Gmono-crePV whose replication in Neuro-2a$^{CD155}$ cells increased by two logs compared to mono-crePV (FIG. 2D/2G) whereas in SK-N-SY5Y and SK-N-MC cells it was less remarkable (FIG. 2B, C). Nomoto and his colleagues have described a related observation before (Shiroki, 1995). PV1(M), while replicating in mouse L$^{CD155}$ cells at 37° C. with wild type kinetics, is highly restricted in these cells at 40° C. (Shiroki, 1995). The temperature sensitive phenotype in mouse cells is ablated by the same $A_{133}G$ transition described here (Shiroki, 1995). It is noteworthy, however, that the host cell restriction of PV1(M) in mouse L$^{CD155}$ cells is apparent only at 40° C. whereas mono-crePV is restricted in Neuro-2a$^{CD155}$ cells already at 37° C. Since a stimulating effect conferred by the $A_{133}G$ mutation is also observed in one of the human neuroblastoma cells of neuronal origin (SK-N-MC), it appears that the $A_{133}G$ transition is not strictly a host range mutation.

The increased replication in Neuro-2a$^{CD155}$ cells of $A_{133}$Gmono-crePV co-varied with an increase of neuropathogenicity in both CD155 tg mice and CD155 tgA/J mice although the virus was still attenuated compared to wt poliovirus (Table 1). By comparing the two other human neuroblastoma cell lines with SK-N-MC cells, it was observed that both mono-crePV and $A_{133}$Gmono-crePV replicate more efficiently in SK-N-SH and SH-SY5Y cells (FIGS. 2A, B and C). Moreover, the temperature sensitive phenotype of mono-cre PV is absent or weak in SK-N-SH or SH-SY5Y cells, respectively (FIGS. 2A, B and C). Interestingly, at 39.5° C., $A_{133}$Gmono-crePV replicated better than mono-crePV in SH-SY5Y, SK-N-MC, and Neuro-2a$^{CD155}$ cells (FIGS. 2A, B and C). These results suggest that the $A_{133}G$ mutation is responsible for an increased replication at 39.5° C. not only in mouse neuroblastoma cells but also in human neuroblastoma cells.

A single intra-tumoral injection of $1\times10^6$ pfu of $A_{133}$Gmono-crePV into four CD155 tgA/J mice, bearing a subcutaneous Neuro-2a$^{CD155}$ tumor, caused dramatic tumor regression within 5 days. However, two of four animals treated with $A_{133}$Gmono-crePV showed paralysis and died approximately 7 days after virus injection (data not shown). This result suggested that $A_{133}$Gmono-crePV can efficiently replicate in subcutaneous neuroblastoma but it can also spread to the CNS causing paralysis.

EXAMPLE 6

Immunization and Microneutralization Assay

Unacceptable side effects of $A_{133}$Gmono-crePV can be prevented by the presence of serum neutralizing antibodies. CD155 tgA/J mice were immunized with mono-crePV ($1\times10^8$ pfu) intraperitoneally three times at one-week intervals (FIG. 3(I)). For the neutralizing antibody assay, blood was collected from the tail vein before immunization and on day 21 after the last immunization. Titers of poliovirus-neutralizing antibodies in mouse serum samples were determined by microneutralization assay with 100 plaque forming unit (pfu) of challenge virus, performed according to the recommendations of WHO (World Health Organization, 1997).

High titers of neutralizing antibodies against poliovirus (in the range of 256-2048) were detectable in all mice at day 21 post-immunization (data not shown). Immunized and control animals were challenged by the intramuscular route with $1\times10^6$ pfu of PV1(M) to examine whether the anti-polio antibodies protected from poliovirus CNS invasion. None of immunized CD155 tgA/J mice showed signs of paresia and paralysis whereas all of the control CD155 tgA/J mice died of flaccid paralysis within 5 days after PV1(M) injection. This result suggests that the large amount of oncolytic virus delivered locally into the tumor escaped the circulating anti-poliovirus antibodies until the substrate for viral proliferation (the tumor cells) was exhausted. Similar observations have been reported with other oncolytic viruses in mice and humans (Nakamura, 2002) (Coffey, 1998) (Nemunaitis, 2000).

EXAMPLE 7

Tumor Treatment Model

Figure 3:
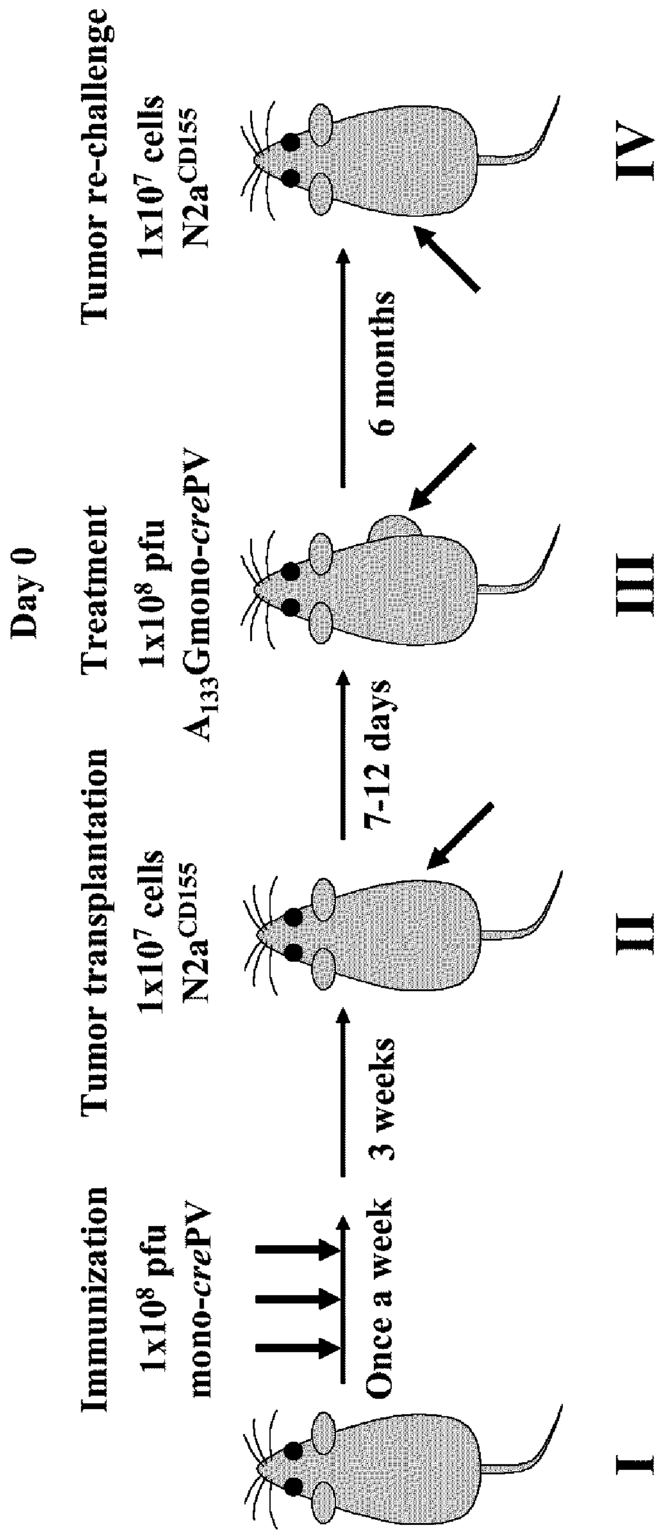
FIG. 3. Schematic presentation of $A_{133}$Gmono-crePV therapy on Neuro-$2a^{CD155}$ tumors in CD155 tgA/J mice with established immunity against poliovirus. Stage I, CD155 tgA/J mice were immunized intraperitoneally with live mono-crePV ($1\times10^8$ pfu) three times with an interval one week. Stage II, 21 days after the last immunization, $1\times10^7$ cells Neuro-$2a^{CD155}$ cells were transplanted subcutaneously the animals given. Stage III, intratumoral treatment of the subcutaneous tumor with $A_{133}$Gmono-crePV ($1\times10^8$ pfu) or PBS at day 0, 2, 4 and 6. Stage IV, mice that survived without signs of tumors for 6 months were re-challenged with Neuro-$2a^{CD155}$ cells ($1\times10^7$ cells) in the contra lateral flank.

Neuro-$2a^{CD155}$ cells ($1\times10^7$) were subcutaneously implanted in the right flank of each CD155 tgA/J immunized mouse (day 21 after the last immunization) (following the schedule outlined in FIG. 3). When the subcutaneous tumor volumes were approximately 170 $mm^3$ (approximately 7-12 days after implantation), mice were inoculated intratumorally with $A_{133}$Gmono-crePV or PBS, respectively. Tumor growth was determined by measuring the tumor volume (length× width×height) every day. Mice were sacrificed when their tumors measured reached >17 mm in any diameter. Mice were followed for up to 6 months after treatment. For experiments of re-challenging with tumor cells those animals that survived without signs of cancer cells for 6 months, survivors were inoculated with $1\times10^7$ Neuro-$2a^{CD155}$ cells in the contra lateral flank. For CD155 expression assays, tumor tissue was suspended in 2 volumes of PBS with 1% of TritonX-100 and a protease inhibitor cocktail (Roche). Tumor tissue was lysed with 8 to 12 strokes of a 15-ml Dounce homogenizer with a type B pestle (Bellco) and incubated on ice for 30 min. Cell debris and nuclei were removed by centrifugation at 8,000×g for 10 min at 4° C. 100 μg of cell lysate was separated on a 10% SDS-PAGE followed by Western blot analysis with CD155-specific antiserum NAEZ-8 (1:5,000)/anti-rabbit horse-radish peroxidase (1:10,000) or anti-actin mouse monoclonal antibody JLA20 (1:1,000)/anti-mouse horse-radish peroxidase (1:10,000).

Figure 4:
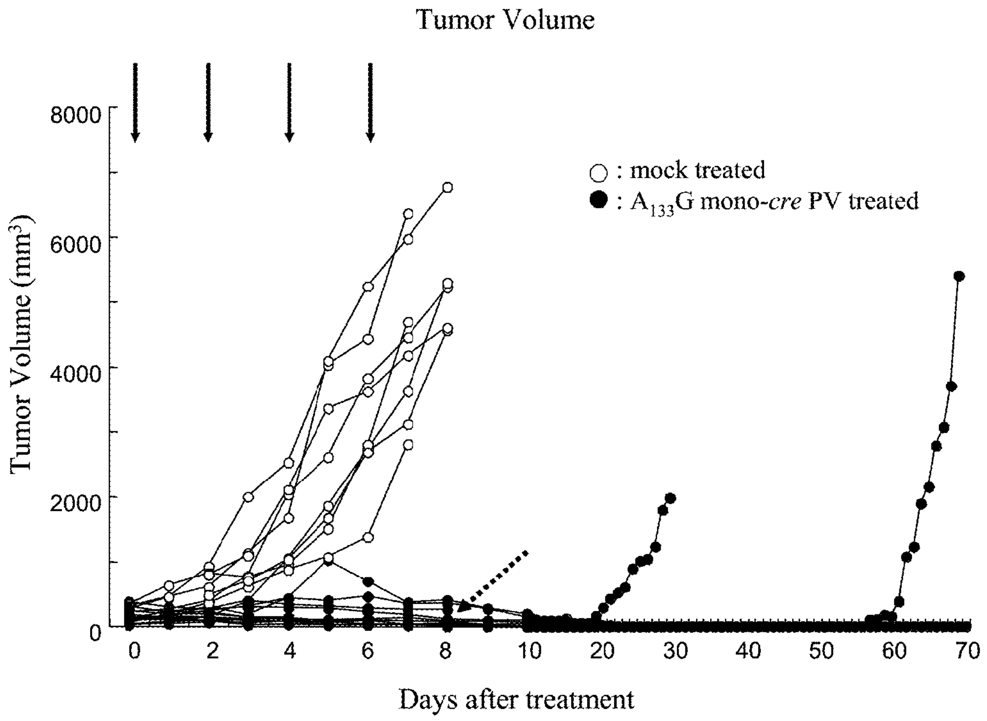
FIG. 4. Abolition of established neuroblastoma implants in CD155 tgA/J mice with $A_{133}$Gmono-crePV. Neuro-$2a^{CD155}$ was introduced as a tumor implant subcutaneously in CD155 tgA/J mice, and multiple intratumoral injections of $1\times10^8$ pfu of $A_{133}$Gmono-crePV (solid arrows) was administered when the tumor volume reached approximately 170 $mm^3$ (day 0). Control animals were given PBS (open circles). Virus-treated animals showed regression of the tumors (closed circles). One of the twelve virus-treated animals was sacrificed at day 8 (dotted arrow) for tumor analysis. Two of the eleven mice observed long term developed tumors as indicated.
Figure 5:
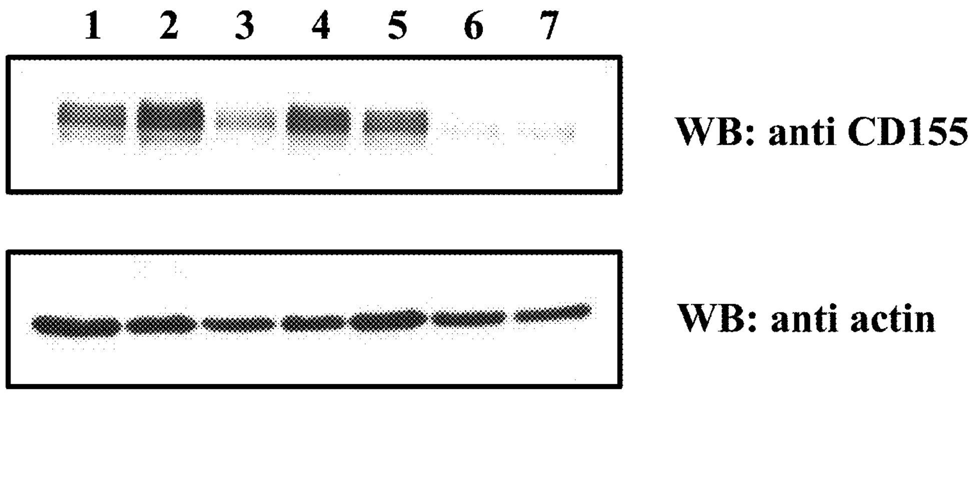
FIG. 5. Expression of CD155 in tumor cells. Whole cell lysates of tumors from mice untreated with $A_{133}$Gmono-crePV (lane 1, 2, 3 and 4), tumor from the mouse which was treated with $A_{133}$Gmono-crePV and sacrificed at day 8 (dotted arrow in FIG. 4) (lane 5) and tumors from two mice with recurrent tumors (lane 6 and 7) were resolved on a 10% SDS-PAGE gel following by Western blotting with anti-CD155 antibody NAEZ-8 (upper panel) or anti-actin antibody (lower panel).

By day 8, the tumors had grown in all PBS-treated mice to a diameter of >17 mm and the animals were euthanized (FIG. 4). In contrast, injection of $A_{133}$Gmono-crePV resulted in marked regression of tumors in all of the twelve treated mice and the mean tumor volume for these virus-treated animals was 128.8 $mm^3$ after 8 days. Moreover, none of $A_{133}$G mono-cre PV treated mice showed paralysis. Of the eleven $A_{133}$Gmono-crePV treated mice, 9 animals showed no evidence of recurrent tumors by day 180. One mouse showed a residual tumor mass, which started growing on day 20. Another mouse, although initially presenting complete regression, showed recurrence of the tumor on day 61. Although the two mice with the recurrent tumors were treated again with $1\times10^8$ pfu of $A_{133}$Gmono-crePV, tumor regression was not observed (data not shown). The two animals were euthanized when the tumor reached a diameter of >17 mm. Western blot analysis with anti-CD155 rabbit polyclonal antibody NAEZ-8 was performed in order to examine CD155 expression in the recurrent tumor cells and harvested tumor from PV treated mice on day 8. Proteins extracted from the tumors that had not been subjected to $A_{133}$Gmono-crePV treatment were used as positive controls. Our results indicated that CD155 expression in the residual and recurrent tumor cells was very low compared with the non-recurrent tumors (FIG. 5).

It is possible that the recurrent tumors resulted from tumor-founding Neuro-$2a^{CD155}$ cells in which expression of CD155 was disrupted, making the tumor cells resistant to $A_{133}$Gmono-crePV. This is highly likely since it has been observed previously that cells transformed to express a foreign gene are likely to produce some rare variants lacking expression of this gene. The nearly undetectable levels of CD155 expression in the two recurrent tumors strongly support this hypothesis (FIG. 5), as selection for the virus resistant cells forming the tumors would be favored. Other unknown mechanisms, e.g. intratumoral heterogeneity, may also have contributed to the observed tumor recurrence. Since most monotherapeutic approaches may not lead to complete tumor control, combination therapy may be needed in the oncolytic treatment of solid tumors, such as neuroblastoma.

EXAMPLE 8

Inhibition of Tumor Recurrence $A_{133}$Gmono-crePV-treated mice with no evidence of recurrent tumors 6 months after virus injection, were re-challenged with Neuro-$2a^{CD155}$ cells (FIG. 3(IV)). Specifically, $1\times10^7$ Neuro-$2a^{CD155}$ cells (the same number of cells as in the original challenge) were injected into the opposite flank of nine animals. Significantly, none of the re-challenged animals developed tumors at the site of Neuro-$2a^{CD155}$ re-inoculation or elsewhere. This data suggests that the oncolytic therapy by $A_{133}$Gmono-crePV activated the immune system against Neuro-$2a^{CD155}$ cells leading to an anti-tumor activity that six months later is likely to be independent of $A_{133}$Gmono-crePV.

EXAMPLE 9

Figure 6:
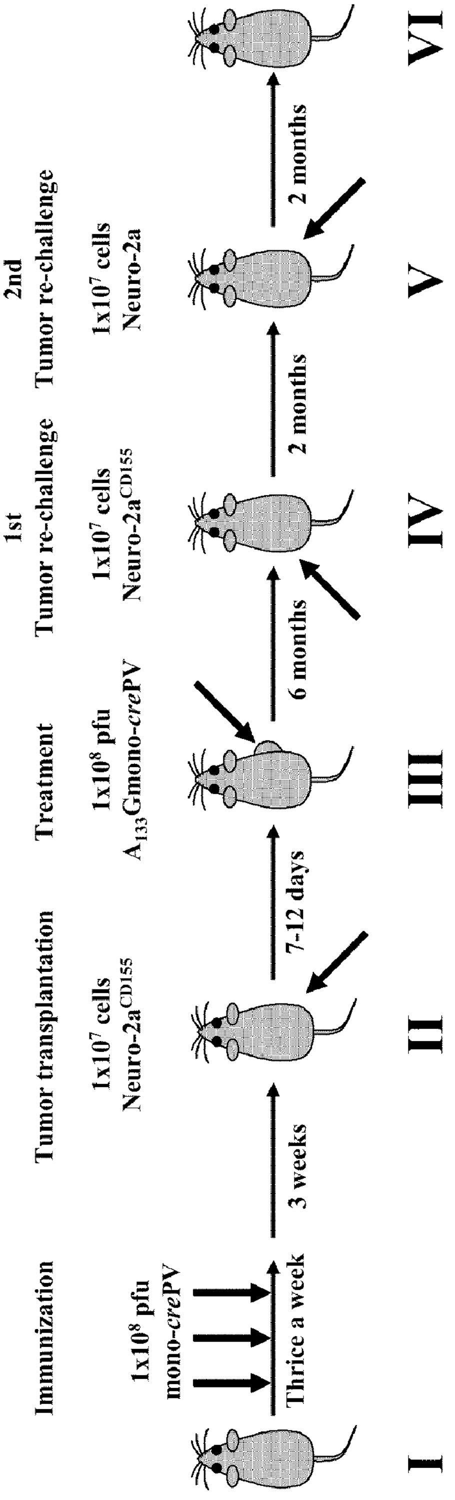
FIG. 6. Schematic presentation of $A_{133}$Gmono-crePV therapy and tumor re-challenge in CD155 tgA/J mice. Stage I, CD155 tgA/J mice were immunized intraperitoneally with live mono-crePV ($1\times10^8$ pfu) three times with an interval one week. Stage II, 21 days after the last immunization, $1\times10^7$ cells Neuro-2a$^{CD155}$ cells were transplanted subcutaneously the animals given. Stage III, intratumoral treatment of the subcutaneous tumor with $A_{133}$Gmono-crePV ($1\times10^8$ pfu) or PBS at day 0, 2, 4 and 6. Stage IV ($1^{st}$ tumor re-challenge), mice that survived without signs of tumors for 6 months were re-challenged with Neuro-2a$^{CD155}$ cells ($1\times10^7$ cells) in the contra lateral flank. Stage V ($2^{nd}$ tumor re-challenge), mice that survived without signs of tumors for 2 months after 1St tumor re-challenge were re-challenged with Neuro-2a cells ($1\times10^7$ cells) in the contra lateral flank. Stage VI, mice were sacrificed 2 months after $2^{nd}$ tumor re-challenge and splenocytes were used for the cytotoxic activity.

Cytotoxicity of Splenocytes from Immune-competent Mice Treated with Intratumoral Injections of $A_{133}$Gmono-crePV To evaluate the cellular anti-tumor immunity induced by oncolytic therapy with live attenuated poliovirus, the cytolytic anti-tumor activity of splenocytes collected from the neuroblastoma-cured CD155 tgA/J mice after consecutive rechallenge with Neuro-$2a^{CD155}$ and Neuro-2a cells (FIG. 6; IV-VI) was quantified. Splenocytes from these mice were isolated 2 months after the last challenge (FIG. 6, VI). As a control group, subcutaneous Neuro-2a$^{CD155}$ tumors were established in polio-immunized CD155 tgA/J mice. These animals were killed after the tumor had reached a volume of ~500 mm$^3$ and their splenocytes were used as a control in cytotoxic assays.

Figure 7:
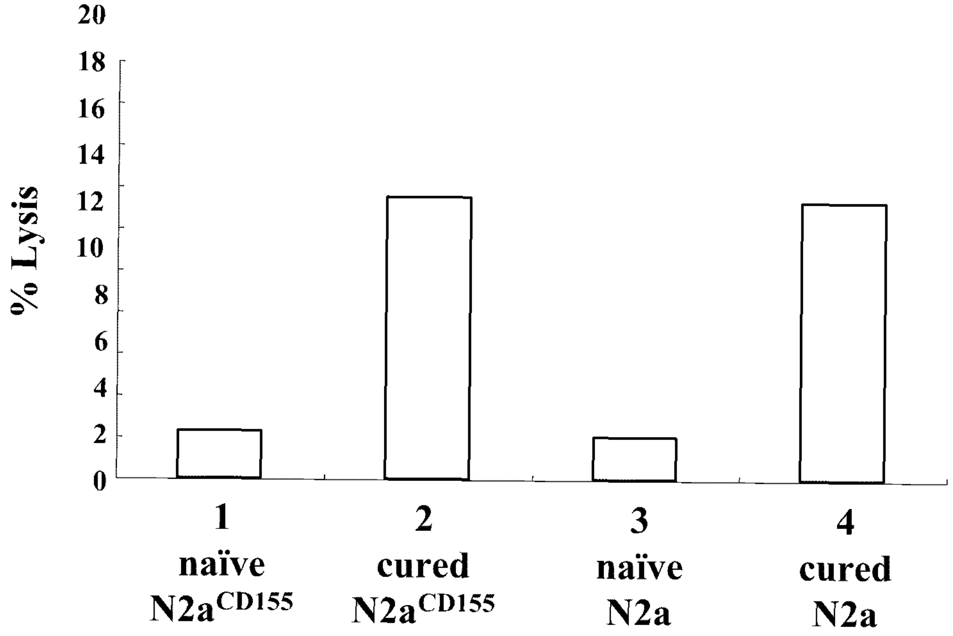
FIG. 7. Tumor-specific cytotoxic T cell activity after virotherapy. (A) Mice were sacrificed 2 months after $2^{nd}$ tumor re-challenge as described in FIG. 6 (VI) and the cytotoxic activity of effector cells prepared from spleens was measured against either Neuro-2a$^{CD155}$ cells or Neuro-2a cells. (B) Characterization of effector cytotoxic cells. Mice were sacrificed 2 months after $2^{nd}$ tumor re-challenge as described in FIG. 6 (VI). Splenocytes purified from the mice were incubated with neutralizing antibody against CD4, CD8, NK or PBS (as control) and then tested for cytotoxicity against Neuro-2a$^{CD155}$ cells.
Figure 7:
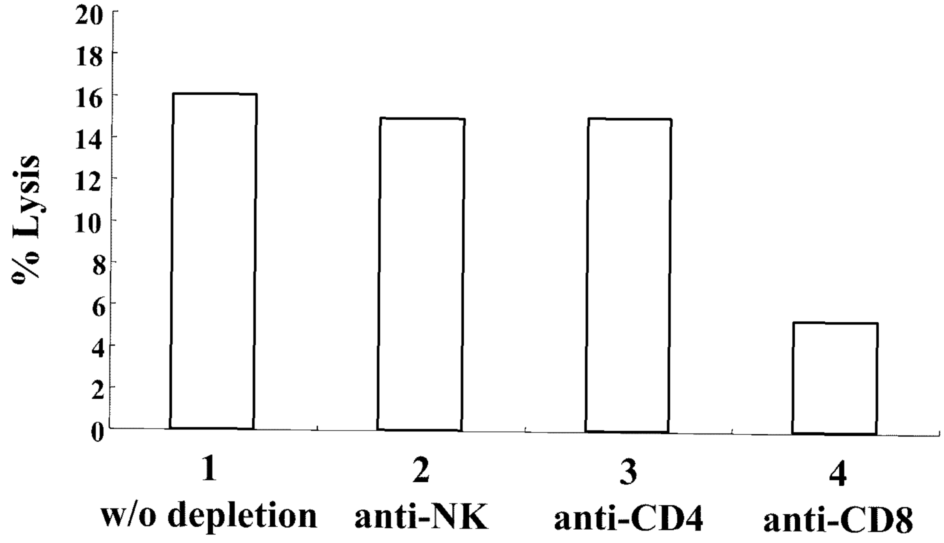

Splenocytes isolated from mice cured from neuroblastoma showed strong lytic activity against both target cells tested (Neuro-2a$^{CD155}$ and Neuro-2a), in contrast to the scant or negligible tumor-specific lysis detected in splenocytes derived from control mice (FIG. 7A). Notably, the cytolytic activity of splenocytes from neuroblastoma-cured mice was similar against both Neuro-2a and Neuro-2a$^{CD155}$ cells, confirming that tumor cell destruction does not require specific interaction of NK cell receptors with the poliovirus receptor (i.e., CD155/CD96/226 interaction).

To determine which cell subpopulations are responsible for the cell-mediated antitumor immune responses, splenocytes from the cured mice were depleted in vitro of NK, CD4$^+$ or CD8$^+$ cells respectively, prior to cytotoxic assay. As shown in FIG. 7B, incubation of splenocytes with neutralizing antibody NK1.1 or anti-CD4 had little or no effect on their ability to kill Neuro-2a$^{CD155}$ cells (FIG. 7B). In contrast, incubation with neutralizing anti-CD8 antibody reduced the cytolytic activity of splenocytes from cured mice (FIG. 7B lane 4), suggesting that cytotoxic CD8$^+$ T cells are the principal mediators of antineuroblastoma immunity elicited by $A_{133}$Gmono-crePV virotherapy.

EXAMPLE 10

Figure 8:
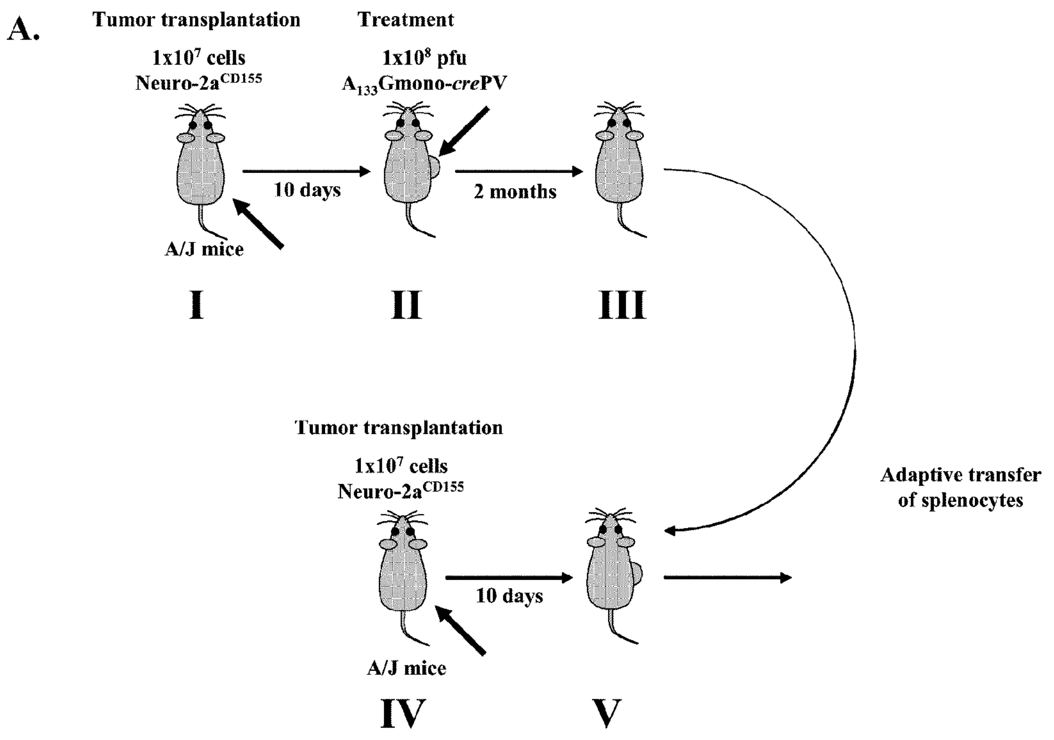
FIG. 8. Antitumor effect of adaptively transferred splenocytes. (A) Schematic presentation of $A_{133}$Gmono-crePV therapy on Neuro-2a$^{CD155}$ tumors in A/J mice against poliovirus. Stage I, $1\times10^7$ cells Neuro-2a$^{CD155}$ cells were transplanted subcutaneously in A/J mice. Stage II, intratumoral treatment of the subcutaneous tumor with $A_{133}$Gmono-crePV ($1\times10^8$ pfu) or PBS at day 0, 2, 4 and 6. Stage III, mice that survived without signs of tumors for 2 months were sacrificed and splenocytes were purified. Stage IV, prior to adoptive transfer of splenocytes, $1\times10^7$ cells Neuro-2a$^{CD155}$ cells were transplanted subcutaneously in A/J mice. Stage V, when the subcutaneous tumor volumes were ~170 mm$^3$, $2\times10^7$ splenocytes in 100 μl of PBS were adaptively transferred to the mice (n=6 mice per group) by tail vein injection. (B) Tumor growth of established neuroblastoma implants in A/J mice. Tumor size was measured once a week and tumor volume was determined.
Figure 8:
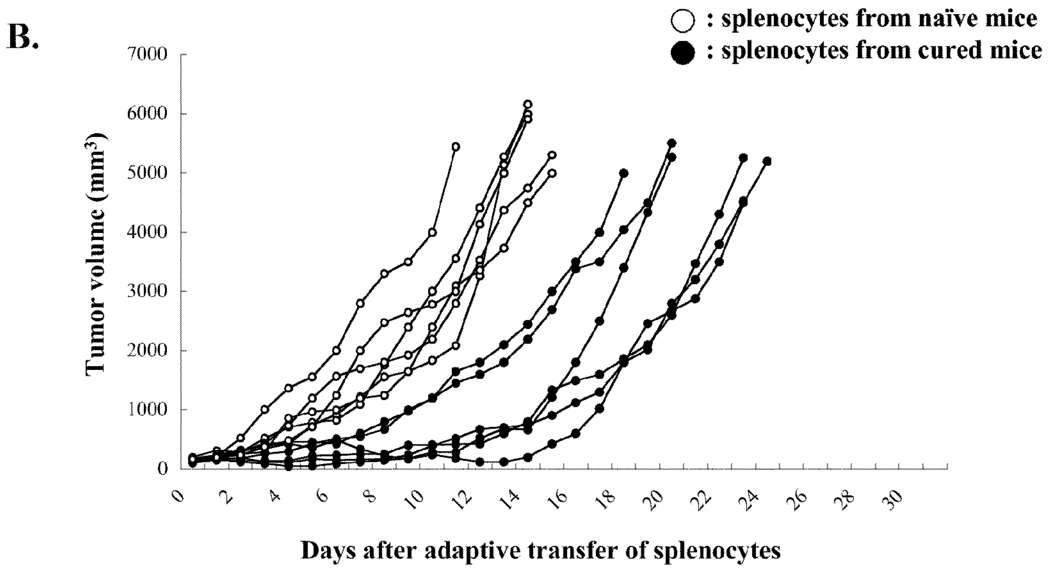

Antitumor Effect of Adoptively Transferred Splenocytes from Cured Mice by $A_{133}$Gmono-crePV Virotherapy $A_{133}$Gmono-crePV-induced antitumor immunity was demonstrated by adoptive transfer of splenocytes harvested from cured A/J mice. The donor mice were naïve A/J mice that had developed ~170 mm$^3$ subcutaneous Neuro-2a$^{CD155}$ tumor (FIG. 8A) and been cured with four injections of $A_{133}$Gmono-crePV into. Splenocytes from naïve A/J mice served as a negative control. Tumor sizes were measured every day and tumor volumes were calculated. As expected, all the control mice experienced progressive tumor growth and sacrificed within 21 days (FIG. 8B). By comparison with the effects of splenocytes from controls, the adaptively transferred splenocytes from $A_{133}$Gmono-crePV-treated mice produced significantly greater inhibition of tumor growth (FIG. 8B). No evidence of overt toxicity was observed by adoptive transfer of splenocytes isolated from cured A/J mice under these conditions. This result indicates that a tumor-specific immune response was induced by virotherapy and oncolysis.

REFERENCES

Berwin, B., Reed, R. C., Nicchitta, C. V. Virally induced lytic cell death elicits the release of immunogenic GRP94/gp96. J Biol Chem 2001; 276:21083-8.

Cello, J., Paul, A. V., Wimmer, E. Chemical synthesis of poliovirus cDNA: generation of infectious virus in the absence of natural template. Science 2002; 297:1016-8.

Cello, J., Toyoda, H., DeJesus, N., Wimmer, E. Growth phenotypes and biosafety profiles in poliovirus receptor transgenic mice of recombinant oncolytic polio/human rhinoviruses. J. Med. Virol. 2008; 80:352-9

Coffey, M. C., Strong, J. E., Forsyth, P. A., Lee, P. W. Reovirus therapy of tumors with activated Ras pathway. Science 1998; 282:1332-4.

DeJesus, N., Franco, D., Paul, A., Wimmer, E., Cello, J. Mutation of a single conserved nucleotide between the cloverleaf and internal ribosome entry site attenuates poliovirus neurovirulence. J Virol 2005; 79:14235-43.

Gromeier, M., Alexander, L., Wimmer, E. Internal ribosomal entry site substitution eliminates neurovirulence in intergeneric poliovirus recombinants. Proc Natl Acad Sci USA 1996; 93:2370-5.

Gromeier, M., Bossert, B., Arita, M., Nomoto, A., Wimmer, E. Dual stem loops within the poliovirus internal ribosomal entry site control neurovirulence. J Virol 1999; 73:958-64.

Gromeier, M., Lachmann, S., Rosenfeld, M. R., Gutin, P. H., Wimmer, E. Intergeneric poliovirus recombinants for the treatment of malignant glioma. Proc Natl Acad Sci USA 2000; 97:6803-8.

Katzenstein, H. M., Cohn, S. L. Advances in the diagnosis and treatment of neuroblastoma. Curr Opin Oncol 1998; 10:43-51.

Kirn, D., Martuza, R. L., Zwiebel, J. Replication-selective virotherapy for cancer: biological principles, risk management, and future directions. Nat Med 2001; 7:781-7.

Koike, S., Taya, C., Kurata, T., et al. Transgenic mice susceptible to poliovirus. Proc Natl Acad Sci USA 1991; 88:951-5.

Kushner, B. H., Cheung, N. K., Kramer, K., Heller, G., Jhanwar, S. C. Neuroblastoma and treatment-related myelodysplasia/leukemia: the Memorial Sloan-Kettering experience and a literature review. J Clin Oncol 1998; 16: 3880-9.

Matthay, K. K., Villablanca, J. G., Seeger, R. C., et al. Treatment of high-risk neuroblastoma with intensive chemotherapy, radiotherapy, autologous bone marrow transplantation, and 13-cis-retinoic acid. Children's Cancer Group. N Engl J Med 1999; 341:1165-73.

Mohr, I. To replicate or not to replicate: achieving selective oncolytic virus replication in cancer cells through translational control. Oncogene 2005; 24:7697-709.

Mueller, S., Wimmer, E. Recruitment of nectin-3 to cell-cell junctions through trans-heterophilic interaction with CD155, a vitronectin and poliovirus receptor that localizes to a(v)h3 integrin-containing membrane microdomains. J Biol Chem 2003; 278:31251-60.

Mueller, S., Wimmer, E., Cello, J. Poliovirus and poliomyelitis: a tale of guts, brains, and an accidental event. Virus Res 2005; 111:175-93.

Nakamura, H., Kasuya, H., Mullen, J. T., et al. Regulation of herpes simplex virus g(1)34.5 expression and oncolysis of diffuse liver metastases by Myb34.5. J Clin Invest 2002; 109:871-82.

Nemunaitis, J., Ganly, I., Khuri, F., et al. Selective replication and oncolysis in p53 mutant tumors with ONYX-015, an ELB-55 kD gene-deleted adenovirus, in patients with advanced head and neck cancer: a phase TI trial. Cancer Res 2000; 60:6359-66.

Obuchi, M., Fernandez, M., Barber, G. N. Development of recombinant vesicular stomatitis viruses that exploit defects in host defense to augment specific oncolytic activity. J Virol 2003; 77:8843-56.

Ochiai, H., Moore, S. A., Archer, G. E., et al. Treatment of intracerebral neoplasia and neoplastic meningitis with regional delivery of oncolytic recombinant poliovirus. Clin Cancer Res 2004; 10:4831-8.

Ochiai, H., Campbell, S. A., Archer, G. E., et al. Targeted therapy for glioblastoma multiforme neoplastic meningitis with intrathecal delivery of an oncolytic recombinant poliovirus. Clin Cancer Res 2006; 12: 1349-54.

Parato, K. A., Senger, D., Forsyth, P. A., Bell, J. C. Recent progress in the battle between oncolytic viruses and tumours. Nat Rev Cancer 2005; 5:965-76.

Paul, A. V. Possible unifying mechanism of picornavirus genome replication. In: Semler B L, Wimmer E, editors. Molecular biology of picornaviruses. Washington (DC): ASM Press; 2002. p. 227-46.

Paul, A. V., Yin, J., Mugavero, J., et al. A "slide-back" mechanism for the initiation of protein-primed RNA synthesis by the RNA polymerase of poliovirus. J Biol Chem 2003; 278:43951-60.

Pincus, S. E., Diamond, D. C., Emini, E. A., Wimmer E. Guanidine-selected mutants of poliovirus: mapping of point mutations to polypeptide 2C. J Virol 1986; 57: 638-46.

Porosnicu, M., Mian, A., Barber, G. N. The oncolytic effect of recombinant vesicular stomatitis virus is enhanced by expression of the fusion cytosine deaminase/uracil phosphoribosyltransferase suicide gene. Cancer Res 2003; 63:8366-76.

Reed, L. J., Muench, H. A simple method of estimating fifty percent endpoint. Am J Hyg 1938; 27:493-7.

Rieder, E., Paul, A. V., Kim, D. W., van Boom, J. H., Wimmer, E. Genetic and biochemical studies of poliovirus cis-acting replication element cre in relation to VPg uridylylation. J Virol 2000; 74:10371-80.

Ring, C. J. Cytolytic viruses as potential anti-cancer agents. J Gen Virol 2002; 83:491-502.

Shiroki, K., Ishii, T., Aoki, T., Kobashi, M., Ohka, S., Nomoto, A. A new cis-acting element for RNA replication within the 5' noncoding region of poliovirus type 1 RNA. J Virol 1995; 69:6825-32.

Solecki, D., Schwarz, S., Wimmer, E., Lipp, M., Bernhardt, G. The promoters for human and monkey poliovirus receptors. Requirements for basic and cell type-specific activity. J Biol Chem 1997; 272:5579-86.

Thome, S. H., Hermiston, T., Kim, D. Oncolytic virotherapy: approaches to tumor targeting and enhancing antitumor effects. Semin Oncol 2005; 32:537-48.

Toyoda, H., Ido, M., Hayashi, T., et al. Experimental treatment of human neuroblastoma using live-attenuated poliovirus. Int J Oncol 2004; 24:49-58.

van der Werf, S., Bradley, J., Wimmer, E., Studier, F. W., Dunn, J. J. Synthesis of infectious poliovirus RNA by purified T7 RNA polymerase. Proc Natl Acad Sci USA 1986; 83:2330-4.

Wahby, A. F. Combined cell culture enzyme-linked immunosorbent assay for quantification of poliovirus neutralization-relevant antibodies. Clin Diagn Lab Immunol 2000; 7:915-9.

Weinstein, J. L., Katzenstein, H. M., Cohn, S. L. Advances in the diagnosis and treatment of neuroblastoma. Oncologist 2003; 8:278-92.

Yin, J., Paul, A. V., Wimmer, E., Rieder E. Functional dissection of a poliovirus cis-acting replication element [PV-cre (2C)]: analysis of single- and dual-cre viral genomes and proteins that bind specifically to PV-cre RNA. J Virol 2003; 77:5152-66.

Young, L. S., Searle, P. F., Onion, D., Mautner, V. Viral gene therapy strategies: from basic science to clinical application. J Pathol 2006; 208:299-318.

The invention claimed is:

1. A method of treating a tumor in a subject, comprising:

administering to the tumor a therapeutically effective amount of a composition comprising a recombinant poliovirus containing a single active cre regulatory element, said cre element located in the spacer region of the 5'-NTR between the cloverleaf and internal ribosome entry site (IRES);

wherein the recombinant poliovirus infects and lyses tumor cells.

2. The method of claim 1, wherein the native cre element in the 2C coding region of the recombinant poliovirus is inactivated by a mutation which does not change the encoded amino acid sequence.

3. The method of claim 1, wherein the recombinant poliovirus comprises an $A_{133}G$ mutation in domain II of the internal ribosome entry site (IRES).

4. The method of claim 1, wherein the recombinant poliovirus comprises SEQ ID NO:1.

5. The method of claim 1, wherein an immune response is elicited against the tumor.

6. The method of any one of claims 1, wherein the recombinant poliovirus is administered by intratumoral injection.

7. The method of any one of claims 1, wherein the subject is first immunized with a poliovirus corresponding in serotype to the recombinant poliovirus.

8. The method of any one of claims 1, wherein the tumor is a malignant tumor.

9. The method of any one of claims 1, wherein the tumor is a neuroblastoma.

10. The method of any one of claims 1, wherein the tumor is a breast tumor, a colorectal tumor, a lung tumor, a gastrointestinal tumor, a liver tumor, a prostate tumor, an adrenal tumor, a pancreatic tumor, or a brain tumor.

* * * * *

UNITED STATES PATENT AND TRADEMARK OFFICE

CERTIFICATE OF CORRECTION

PATENT NO. : 8,066,983 B2
APPLICATION NO. : 12/405068
DATED : November 29, 2011
INVENTOR(S) : Wimmer et al.

It is certified that error appears in the above-identified patent and that said Letters Patent is hereby corrected as shown below:

Column 1, paragraph 2 of the patent, please replace the Federal Funding paragraph with the following:

-- FEDERAL FUNDING --

--This invention was made with government support under grant numbers AI394850 and AI151223 awarded by the National Institute of Health. The government has certain rights in the invention--

Signed and Sealed this
Seventeenth Day of January, 2012

David J. Kappos
*Director of the United States Patent and Trademark Office*